United States Patent
Kuwabara et al.

(10) Patent No.: US 9,796,727 B2
(45) Date of Patent: Oct. 24, 2017

(54) FIELD EFFECT TRANSISTOR

(75) Inventors: Hirokazu Kuwabara, Tokyo (JP); Masaaki Ikeda, Tokyo (JP); Kazuo Takimiya, Higashihiroshima (KR)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 223 days.

(21) Appl. No.: 13/203,494

(22) PCT Filed: Feb. 25, 2010

(86) PCT No.: PCT/JP2010/052923
§ 371 (c)(1),
(2), (4) Date: Aug. 26, 2011

(87) PCT Pub. No.: WO2010/098372
PCT Pub. Date: Sep. 2, 2010

(65) Prior Publication Data
US 2011/0303910 A1  Dec. 15, 2011

(30) Foreign Application Priority Data

Feb. 27, 2009 (JP) ................................ 2009-047298
Dec. 21, 2009 (JP) ................................ 2009-289818

(51) Int. Cl.
| | | |
|---|---|---|
| C07C 319/14 | (2006.01) | |
| C07C 323/22 | (2006.01) | |
| C07D 495/04 | (2006.01) | |
| H01L 51/00 | (2006.01) | |
| H01L 51/05 | (2006.01) | |

(52) U.S. Cl.
CPC .......... C07D 495/04 (2013.01); C07C 319/14 (2013.01); H01L 51/0005 (2013.01); H01L 51/0074 (2013.01); H01L 51/0541 (2013.01); H01L 51/0545 (2013.01)

(58) Field of Classification Search
CPC . C09K 11/06; H01L 51/0072; H01L 51/5016; H05B 33/14; Y02E 10/549; C07D 33/50; C07D 495/04
USPC ........ 438/99, 478; 257/40, E21.025, E21.09, 257/E51.025, 66; 549/200
See application file for complete search history.

(56) References Cited

U.S. PATENT DOCUMENTS

| | | | |
|---|---|---|---|
| 9,018,630 | B2 * | 4/2015 | Takimiya .............. C07C 319/20 257/66 |
| 2006/0052612 | A1 | 3/2006 | Stossel et al. |
| 2009/0043113 | A1 * | 2/2009 | Park et al. ...................... 549/41 |
| 2010/0032655 | A1 | 2/2010 | Takimiya et al. |
| 2010/0065826 | A1 | 3/2010 | Takimiya et al. |
| 2013/0330876 | A1 | 12/2013 | Takimiya et al. |

FOREIGN PATENT DOCUMENTS

| | | |
|---|---|---|
| CN | 1671675 A | 9/2005 |
| CN | 101528753 A | 9/2009 |
| CN | 101529609 B | 10/2010 |
| CN | 102333780 A | 1/2012 |
| EP | 1138328 A1 | 10/2001 |
| EP | 1847544 A1 | 10/2007 |
| EP | 2077590 A1 | 7/2009 |
| EP | 2098527 A1 * | 9/2009 |
| JP | 6-177380 A | 6/1994 |
| JP | 2001-94107 A | 4/2001 |
| JP | 2008-10541 A | 1/2008 |
| JP | 2009-152355 A | 7/2009 |
| JP | 2009-196975 A | 9/2009 |
| JP | 2010-258214 A | 11/2010 |
| KR | 20080100982 A | 11/2008 |
| KR | 2009-0074248 A | 7/2009 |
| WO | 2006/077888 A1 | 7/2006 |
| WO | 2008/047896 A1 | 4/2008 |
| WO | 2008/050726 A1 | 5/2008 |
| WO | WO 2008050726 A1 * | 5/2008 |
| WO | 2009/009790 A1 | 1/2009 |
| WO | 2010/098372 A1 | 9/2010 |

OTHER PUBLICATIONS

Kazuo Takimiya Novel Fused-Ring Aromatic Compound Process for Producing the Same and Use Thereof Feb. 5, 2008 WO 2008050726 A1.*
Notice of Allowance dated Jan. 8, 2015 in co-pending U.S. Appl. No. 14/000,440.
Extended European Search Report dated May 18, 2012 in corresponding European patent application No. EP 10746251.7, 8 pages.
International Search Report and Written Opinion dated Mar. 27, 2012 in co-pending PCT application No. PCT/JP2012/054604.
International Preliminary Report on Patentability dated Sep. 6, 2013 in co-pending PCT application No. PCT/JP2012/054604.
European communication dated Jun. 16, 2014 in co-pending European patent application No. EP 12750215.1.
English translation of Chinese communication, dated Aug. 8, 2014 in co-pendng Chinese patent application No. CN 201280010570.8.
Eur. J. Org. Chem., 2002, No. 2, pp. 319-326, "Developments in the Simmons-Smith-Mediated Epoxidation Reaction", Aggarwal, et al.
Tetrahedron Letters, 1988, vol. 29, No. 23, pp. 2783-2786, "Palladium(0) Catalyzed Coupling of trans-1,2-Bis(tri-n-butylstannyl)ethylene with Aromatic Halides: A Convenient Synthesis of Substituted trans-B-Bromostyrenes", Haack, et al.

(Continued)

Primary Examiner — Niloofar Rahmani
(74) Attorney, Agent, or Firm — Nields, Lemack & Frame, LLC

(57) ABSTRACT

A heterocyclic compound represented by formula (1) and a field effect transistor having a semiconductor layer comprising the compound. (In the formula, $X^1$ and $X^2$ each independently represents a sulfur atom or a selenium atom, and $R^1$ and $R^2$ each independently represents a $C_{5-16}$ alkyl.)

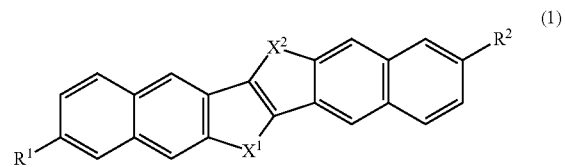

(1)

28 Claims, 3 Drawing Sheets

(56) References Cited

OTHER PUBLICATIONS

Advanced Materials, 2011, vol. 23, No. 10, published online Aug. 20, 2010, XP 55121923, pp. 1222-1225, "Alkylated Dinaphtho[2,3-b:2',3'-f]Thieno[3,2-b]Thiophenes (Cn-DNTTs): Organic Semiconductors for High-Performance Thin-Film Transistors", Kang, et al.
Chemical Science, 2010, vol. 1, No. 2, Received Jan. 30, 2010, Accepted Mar. 26, 2010, published May 20, 2010, XP 55121919, pp. 179-183, "Unique three-dimensional (3D) molecular array in dimethyl-DNTT crystals: a new approach to 3D organic semiconductors", Kang, et al.
Advanced Materials, 2011, vol. 23, No. 14, published online Feb. 10, 2011, XP 55121933, pp. 1626-1629, "Patternable Solution-Crystallized Organic Transistors with High Charge Carrier Mobility", Nakayama, et al.
Applied Physics Letters, American Institute of Physics, 2009, vol. 94, No. 10, published online Mar. 13, 2009, XP 012118363, pp. 103307-1--103307-3, "Three-dimensional organic field-effect transistors with high output current and high on-off ratio", Uno, et al.
Applied Physics Letters, American Institute of Physics, 2009, vol. 94, No. 22, published online Jun. 5, 2009, XP 012121523, pp. 223308-1--223308-3, "Moderately anisotropic field-effect mobility in dinaphtho[2,3-b:2',3'-f]thiopheno [3,2-b]thiophenes single-crystal transistors", Uno, et al.
Notice of Allowance dated Oct. 1, 2014 in co-pending U.S. Appl. No. 14/000,440.
Notice of Allowance dated Oct. 16, 2014 in co-pending U.S. Appl. No. 14/000,440.
International Search Report dated Apr. 13, 2010 in corresponding PCT application No. PCT/JP2010/052923, 4 pages.
Journal of the American Chemical Society, 2007, V. 129, No. 8, pp. 2224-2225, "Facile Synthesis of Highly pi-Extended Heteroarenes, Dinaphtho[2,3-b:2'3'-f]chalcogenopheno[3,2-b]chalcogenophenes, and Their Application to Field-Effect Transistors", Yamamoto, et al.
Advanced Materials, 2008, vol. 20, No. 18, pp. 3388-3392, "Molecular Ordering of High-Performance Soluble Molecular Semiconductors and Re-evaluation of Their Field-Effect Transistor Characteristics", Izawa, et al.
Journal of the American Chemical Society, 2007, V. 129, No. 51, pp. 15732-15733, Highly Soluble [1]Benzothieno[3.2-b]benzothiophene (BTBT) Derivatives for High-Performance, Solution-Processed Organic Field-Effect Transistors, Ebata, et al.
Japanese communication dated Nov. 13, 2013 in corresponding Japanese patent application No. JP 2011-501631.
Partial English translation of Japanese communication dated Nov. 13, 2013 in corresponding Japanese patent application No. JP 2011-501631.
English translation of Written Opinion dated Apr. 13, 2010 in corresponding PCT application No. PCT/JP2010/052923.
English translation of International Preliminary Report on Patentability dated Nov. 13, 2011 in corresponding PCT application No. PCT/JP2010/052923.
Chinese communication, with English translation, dated Apr. 22, 2013 in corresponding Chinese patent application No. CN 201080009791.4.
European communication dated Nov. 24, 2014 in corresponding European patent application No. 10746251.7.
Chinese communication dated Mar. 23, 2016 in co-pending Chinese patent application No. 201410836711.2.
European communication dated May 6, 2015 in co-pending European patent application No. 14198144.9.
European communication dated May 24, 2016 in co-pending European patent application No. 12750215.1.

* cited by examiner

A

B

C

D

E

FIELD EFFECT TRANSISTOR

TECHNICAL FIELD

The present invention relates to a field effect transistor. More specifically, the present invention relates to a field effect transistor characterized by having a semiconductor layer made of a specific organic heterocyclic compound.

BACKGROUND ART

A field effect transistor is a device generally having a semiconductor layer (a semiconductor film), a source electrode, a drain electrode, a gate electrode opposed to these electrodes via an insulating layer, and others on a substrate. The field effect transistor has been widely used not only as a logical circuit element in integrated circuits but also as a switching element or the like. A semiconductor layer is usually made of a semiconductor material. At present, inorganic semiconductor materials mainly including silicon have been used in field effect transistors. Particularly, a thin-film transistor having a semiconductor layer formed from amorphous silicon on a substrate of glass or the like has been used in displays and others. In the case of using such inorganic semiconductor materials, treatments at high temperature or in vacuum are required during manufacturing of field effect transistors. Accordingly, expensive equipment investment and high energy consumption are required for manufacturing, resulting in extremely high costs. In addition, since these materials are exposed to high temperature during manufacturing of field effect transistors, materials having insufficient heat resistance, e.g., a film or a plastic, cannot be used as a substrate. Consequently, a flexible material having bendability or the like cannot be used as a substrate, resulting in the limited applications thereof.

Meanwhile, research and development of field effect transistors with an organic semiconductor material have been actively performed. Use of an organic material enables manufacture by a low-temperature process requiring no treatment at high temperature, extending the range of materials that can be used for a substrate. As a result, it is feasible to manufacture more flexible, lighter and more irrefrangible field effect transistors than were possible. Furthermore, in a manufacturing process of field effect transistors, an application method using a solution of a semiconductor material and a printing method with inkjet or the like can be employed in some instances. Accordingly, large-area field effect transistors may be manufactured at a low cost. Moreover, because various types of compounds can be selected for an organic semiconductor material, it has been expected to develop novel functions based on the characteristics thereof.

Various studies have been conducted so far on use of an organic compound as a semiconductor material. For example, semiconductor materials from a pentacene, a thiophene, or an oligomer or a polymer thereof have been already known as ones having hole transport characteristics (see Patent Documents 1 and 2). Pentacene is an acene-type aromatic hydrocarbon having 5 linearly-fused benzene rings. A field effect transistor using a pentacene as a semiconductor material has been reported to have equivalent charge mobility (carrier mobility) to that of amorphous silicon in practical use. However, field effect transistors with a pentacene are environmentally-degradable and questioned in stability. The same problems are also caused when a thiophene compound is used. Accordingly, neither of the compounds would be highly useful in practice. Under the circumstances, dinaphtho[2,3-b:2',3'-f]thieno[3,2-b]thiophene (DNTT) with high stability in the air was developed and is receiving attention (see Patent Document 3 and Non Patent Document 1).

However, even higher carrier mobility is required for use of these compounds in display application such as organic EL, and improvement in solubility is also required for producing a field effect transistor by an application method such as printing, which also reflects strong market demands. Furthermore, from the viewpoint of durability, development of an organic semiconductor material having high quality and high performance is required. According to prior art on DNTT derivatives having a substituent group such as Patent Documents 3, 4, and 5, examples of the specific substituent groups include a methyl group, a hexyl group, an alkoxy group, and a substituted ethynyl group, and only the methyl group and the substituted ethynyl group are disclosed as a substituent group of the DNTT derivatives in examples, each only exhibiting semiconductor characteristics that are similar to or poorer than those of the DNTT having no substituent group under the present circumstances.

PRIOR ART DOCUMENT

Patent Document

Patent Document 1: JP 2001-94107 A
Patent Document 2: JP 6-177380 A
Patent Document 3: WO 2008/050726
Patent Document 4: JP 2008-10541 A
Patent Document 5: KR 2008100982

Non Patent Document

Non Patent Document 1: J. Am. Chem. Soc., Vol. 129, 2224-2225 (2007)

SUMMARY OF INVENTION

Problem to be Solved by the Invention

An object of the present invention is to provide an organic compound having practical semiconductor characteristics such as excellent carrier mobility; a semiconductor material comprising the compound; and a field effect transistor having a semiconductor layer made of the compound and a method for manufacturing the same.

Solution to Problem

The present inventors conducted studies with a view to solving the aforementioned problems, and have found that dinaphtho[2,3-b:2',3'-f]thieno[3,2-b]thiophene (DNTT) having a C5-C16 alkyl group has excellent characteristics compared to conventional organic semiconductor materials in respect to the aforementioned problems. The present inventors also have found that when the heterocyclic compound is used, a field effect transistor device having distinctly enhanced semiconductor characteristics is produced without influence caused by conditions of a substrate or an insulating film during manufacturing period of the device (or regardless of the presence or absence of treatment of the substrate) and, in addition, that the effect is significantly enhanced by performing heat treatment during manufacturing period of the device. The present invention has been accomplished based on these findings.

Thus, according to an embodiment of the present invention, there are provided (1) A heterocyclic compound represented by the following Formula (1):

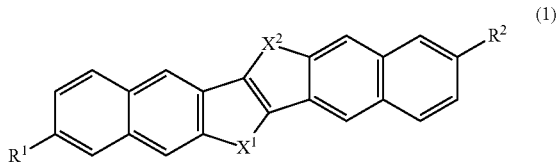

wherein $X^1$ and $X^2$ each independently represent a sulfur atom or a selenium atom, and $R^1$ and $R^2$ each independently represent a C5-C16 alkyl group;

(2) The heterocyclic compound according to item (1), wherein $R^1$ and $R^2$ of Formula (1) each independently represent a linear C5-C16 alkyl group;

(3) The heterocyclic compound according to item (1), wherein $R^1$ and $R^2$ of Formula (1) each independently represent a branched C5-C16 alkyl group;

(4) The heterocyclic compound according to any one of items (1) to (3), wherein $R^1$ and $R^2$ of Formula (1) each independently represent a C6-C14 alkyl group;

(5) The heterocyclic compound according to any one of items (1) to (4), wherein each of $X^1$ and $X^2$ of Formula (1) represents a sulfur atom;

(6) A method for manufacturing an intermediate compound represented by Formula (B) in producing a heterocyclic compound represented by the following Formula (1), comprising the steps of mixing a compound represented by Formula (A) with an alkyl metal reagent such as butyllithium; and further adding dimethyl disulfide, or selenium and methyl iodide thereto:

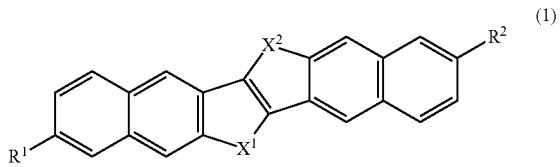

wherein $X^1$ and $X^2$ each independently represent a sulfur atom or a selenium atom, and $R^1$ and $R^2$ each independently represent a C5-C16 alkyl group;

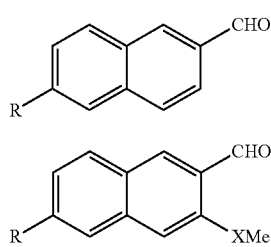

wherein X represents a sulfur atom or a selenium atom, and R represents a C5-C16 alkyl group;

(7) A method for producing the heterocyclic compound represented by the following Formula (1) according to item (1), comprising the steps of reacting intermediates represented by the following Formula (B) with one another to produce a compound represented by Formula (C); and subsequently reacting the compound represented by Formula (C) with iodine:

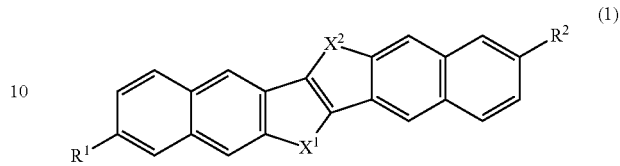

wherein $X^1$ and $X^2$ each independently represent a sulfur atom or a selenium atom, and $R^1$ and $R^2$ each independently represent a C5-C16 alkyl group;

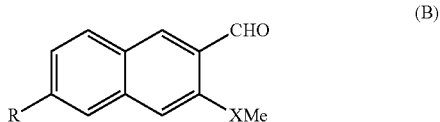

wherein X represents a sulfur atom or a selenium atom, and R represents a C5-C16 alkyl group;

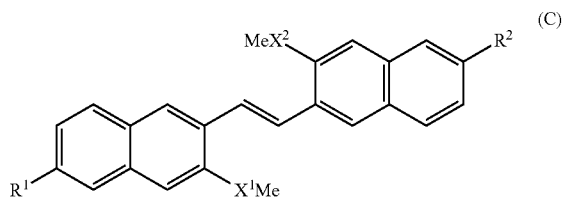

wherein $X^1$ and $X^2$ each independently represent a sulfur atom or a selenium atom, and $R^1$ and $R^2$ each independently represent a C5-C16 alkyl group;

(8) An organic semiconductor material comprising at least one heterocyclic compound according to any one of items (1) to (5);

(9) An ink for use in producing a semiconductor device, comprising the heterocyclic compound according to any one of items (1) to (5);

(10) A field effect transistor having a semiconductor layer comprising at least one heterocyclic compound represented by the following Formula (1):

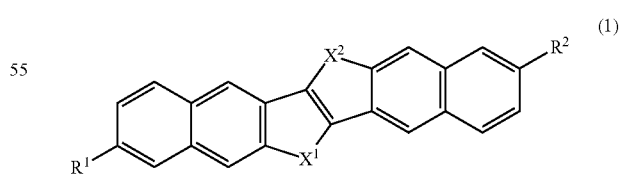

wherein $X^1$ and $X^2$ each independently represent a sulfur atom or a selenium atom, and $R^1$ and $R^2$ each independently represent a C5-C16 alkyl group;

(11) The field effect transistor according to item (10), wherein the field effect transistor is of bottom-contact type;

(12) The field effect transistor according to item (10), wherein the field effect transistor is of top-contact type;

(13) The field effect transistor according to any one of items (10) to (12), further comprising a gate electrode, a gate insulating film, a source electrode, and a drain electrode, wherein the gate insulating film is an organic insulating film.

(14) A method for producing a field effect transistor, comprising the step of forming a semiconductor layer comprising at least one heterocyclic compound represented by the following Formula (1) on a substrate:

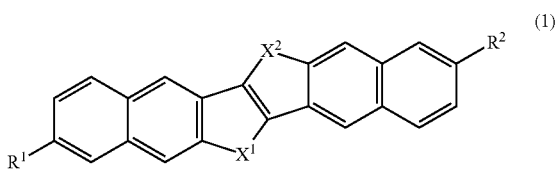

wherein $X^1$ and $X^2$ each independently represent a sulfur atom or a selenium atom, and $R^1$ and $R^2$ each independently represent a C5-C16 alkyl group;

(15) The method for producing the field effect transistor according to item (14), wherein the semiconductor layer is formed by a vapor deposition method;

(16) The method for producing the field effect transistor according to item (14), wherein the semiconductor layer is formed by applying the heterocyclic compound represented by Formula (1) according to item (1) dissolved in an organic solvent;

(17) The method for producing the field effect transistor according to any one of items (14) to (16), wherein the semiconductor layer is heat-treated, after the semiconductor is formed;

(18) A fine particle of the heterocyclic compound represented by Formula (1) according to item (1);

(19) The fine particle according to item (18), wherein the average particle diameter is 5 nm or more and 50 μm or less;

(20) A method for producing the fine particle according to item (18) or (19), wherein the fine particle is precipitated by cooling a solution of the heterocyclic compound dissolved in an organic solvent or by mixing the solution with a solvent;

(21) The method for producing the fine particle according to item (18) or (19), wherein the fine particle is precipitated by mixing a solution of the heterocyclic compound dissolved in an organic solvent with a polar solvent;

(22) The method for producing the fine particle according to item (20), wherein the organic solvent for dissolving the heterocyclic compound has a boiling point of 100° C. or more;

(23) A dispersion of the fine particle of the heterocyclic compound, wherein the fine particle according to item (18) or (19) is dispersed in a solvent;

(24) A method for producing the dispersion according to item (23), wherein the method comprises the step of dispersing the fine particle according to item (18) or (19) in a solvent by mechanical stress;

(25) An ink for use in producing a semiconductor device comprising the fine particle according to item (18) or (19) or the dispersion according to item (23);

(26) The method for producing the field effect transistor according to item (14), wherein the semiconductor layer is formed by applying the ink for use in producing the semiconductor device according to item (25); and

(27) The method for producing the field effect transistor according to item (26), wherein the semiconductor layer is heat-treated, after the semiconductor layer is formed.

Advantageous Effects of Invention

In Formula (1), dinaphtho[2,3-b:2',3'-f]thieno[3,2-b]thiophene (DNTT) with $R^1$ and $R^2$ having a specific C5-C16 alkyl group has more excellent characteristics compared to conventional organic semiconductor materials as described above. More specifically, an organic field effect transistor having distinctly enhanced carrier mobility or the like is provided without influence caused by conditions of a substrate during manufacturing of the device with the heterocyclic compound (or regardless of the presence or absence of treatment of the substrate), by performing heat treatment during manufacturing of the device. Also, a field effect transistor having similarly excellent characteristics can be produced by a film forming process of applying type.

DESCRIPTION OF EMBODIMENTS

Figure 1:
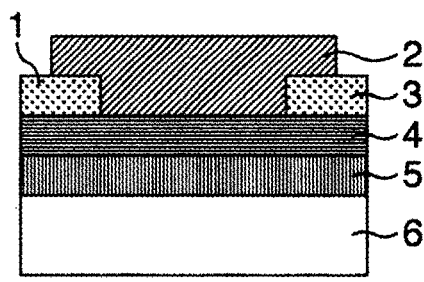
FIG. 1 shows schematic views illustrating the structures of field effect transistors according to embodiments of the present invention.
Figure 1:
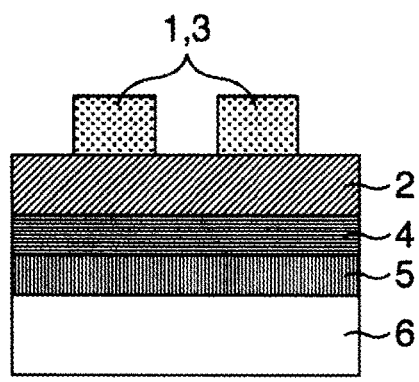
Figure 1:
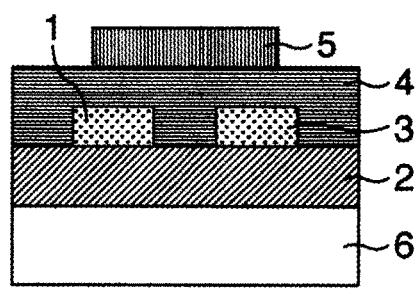
Figure 1:
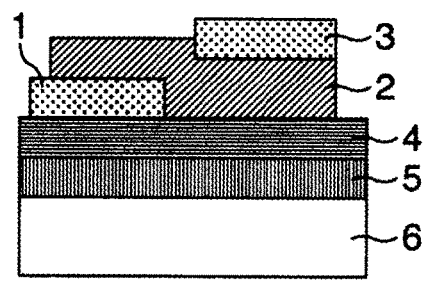
Figure 1:
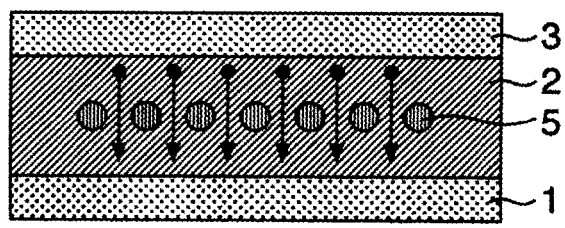

The present invention will be more specifically described.

The present invention relates to an organic field effect transistor with a specific organic compound as a semiconductor material. Specifically, it relates to an organic field effect transistor having a semiconductor layer formed of a compound represented by Formula (1) as the semiconductor material. Firstly, the compound of Formula (1) will be described.

In Formula (1), $X^1$ and $X^2$ each independently represent a sulfur atom or a selenium atom, and $R^1$ and $R^2$ each independently represent a C5-C16 alkyl group.

$X^1$ and $X^2$ are each independently a sulfur atom or a selenium atom, preferably a sulfur atom. Furthermore, $X^1$ and $X^2$ each is more preferably the same, and further preferably the same and a sulfur atom.

Examples of the alkyl group represented by $R^1$ and $R^2$ include a linear, branched or cyclic alkyl group, and the number of carbon atoms thereof is 5 to 16, preferably 6 to 14, more preferably 8 to 12, and further preferably 10.

Examples of the linear alkyl group include n-pentyl, n-hexyl, n-heptyl, octyl, nonyl, decyl, undecyl, dodecyl, tridecyl, tetradecyl, pentadecyl, and hexadecyl.

Examples of the branched alkyl group include a C5-C16 saturated branched alkyl group such as i-hexyl or i-decyl.

Examples of the cyclic alkyl group include a C5-C16 cycloalkyl group such as cyclohexyl, cyclopentyl, adamantyl, or norbornyl.

The C5-C16 alkyl group is preferably a saturated alkyl group rather than an unsaturated alkyl group, and preferably an unsubstituted group rather than a substituted group.

A C6-C14 saturated linear alkyl group is more preferable, a C8-C12 saturated linear alkyl group is further preferable, octyl, decyl, or dodecyl is particularly preferable, and decyl is most preferable.

$R^1$ and $R^2$ each independently represent the alkyl group described above, and may be the same or different, more preferably the same.

A compound having a combination of the atoms and the groups mentioned as preferable examples of the $X^1$, $X^2$, $R^1$ and $R^2$ is more preferable, a compound having a combination of the atoms and the groups mentioned as more preferable examples is further preferable, and a compound having a combination of the atoms and the groups mentioned as further preferable examples is particularly preferable.

The compound represented by Formula (1) can be synthesized by known methods disclosed in Patent Document 3 and Non Patent Document 1 or others. For example, as shown in the following Scheme 1, 2-alkyl-7-methylthio-6-naphthoaldehyde of the following Formula (B) is produced from 2-alkyl-6-naphthoaldehyde represented by the following Formula (A), and then condensed into 1,2-bis(2-alkyl-7-methylthio-6-naphthyl)ethylene of the following Formula (C). Further, the objective compound of 2,9-alkyldinaphtho[2,3-b:2',3'-f]thieno[3,2-b]thiophene of the following Formula (D) can be produced by a ring-closing reaction. More specifically, for example, the compound (B) is produced by reacting the compound (A) with dimethylsulfide, and then, the condensed matter (C) is produced by McMurry coupling. Further, the ring-closing reaction is performed in chloroform using iodine to produce the objective matter (D).

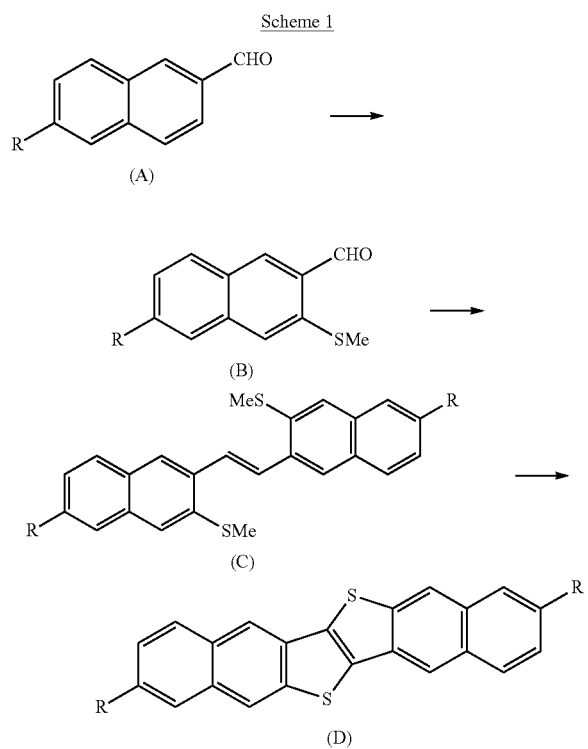

Scheme 1

A method for purifying the compound represented by Formula (1), not being particularly limited, includes known processes such as recrystallization, column chromatography and vacuum sublimation purification. If necessary, these processes may be used in combination.

Examples of the compound represented by Formula (1) are shown in Table 1. Here, "n" represents normal, "i" represents iso, "s" represents secondary, "t" represents tertiary, and "cy" represents cyclo.

TABLE 1

| Compound number | $X^1$ | $X^2$ | $R^1$ | $R^2$ |
|---|---|---|---|---|
| 1 | S | S | n-$C_5H_{11}$ | i-$C_5H_{11}$ |
| 2 | S | S | i-$C_5H_{11}$ | i-$C_5H_{11}$ |
| 3 | S | S | s-$C_5H_{11}$ | s-$C_5H_{11}$ |
| 4 | S | S | t-$C_5H_{11}$ | t-$C_5H_{11}$ |
| 5 | S | S | n-$C_5H_{11}$ | n-$C_5H_{11}$ |
| 6 | S | S | n-$C_6H_{13}$ | n-$C_6H_{13}$ |
| 7 | S | S | i-$C_6H_{13}$ | i-$C_6H_{13}$ |
| 8 | S | S | n-$C_7H_{15}$ | n-$C_7H_{15}$ |
| 9 | S | S | i-$C_7H_{15}$ | i-$C_7H_{15}$ |
| 10 | S | S | $C_8H_{17}$ | $C_8H_{17}$ |
| 11 | S | S | $C_9H_{19}$ | $C_9H_{19}$ |
| 12 | S | S | $C_{10}H_{21}$ | $C_{10}H_{21}$ |
| 13 | S | S | $C_{11}H_{23}$ | $C_{11}H_{23}$ |
| 14 | S | S | $C_{12}H_{25}$ | $C_{12}H_{25}$ |
| 15 | S | S | $C_{13}H_{27}$ | $C_{13}H_{27}$ |
| 16 | S | S | $C_{14}H_{29}$ | $C_{14}H_{29}$ |
| 17 | S | S | $C_{15}H_{31}$ | $C_{15}H_{31}$ |
| 18 | S | S | $C_{16}H_{33}$ | $C_{16}H_{33}$ |
| 19 | S | S | $C_8H_{17}$ | $C_{12}H_{25}$ |
| 20 | S | S | $C_{10}H_{21}$ | $C_{12}H_{25}$ |
| 21 | S | S | $C_8H_{17}$ | $C_{10}H_{21}$ |
| 22 | Se | Se | n-$C_6H_{13}$ | n-$C_6H_{13}$ |
| 23 | Se | Se | i-$C_6H_{13}$ | i-$C_6H_{13}$ |
| 24 | Se | Se | $C_7H_{15}$ | $C_7H_{15}$ |
| 25 | Se | Se | $C_8H_{17}$ | $C_8H_{17}$ |
| 26 | Se | Se | $C_9H_{19}$ | $C_9H_{19}$ |
| 27 | Se | Se | $C_{10}H_{21}$ | $C_{10}H_{21}$ |
| 28 | Se | Se | $C_{11}H_{23}$ | $C_{11}H_{23}$ |
| 29 | Se | Se | $C_{12}H_{25}$ | $C_{12}H_{25}$ |
| 30 | Se | Se | $C_{13}H_{27}$ | $C_{13}H_{27}$ |
| 31 | Se | Se | $C_{14}H_{29}$ | $C_{14}H_{29}$ |
| 32 | Se | Se | $C_{15}H_{31}$ | $C_{15}H_{31}$ |
| 33 | Se | Se | $C_{16}H_{33}$ | $C_{16}H_{33}$ |
| 34 | S | Se | $C_8H_{17}$ | $C_8H_{17}$ |
| 35 | S | Se | $C_9H_{19}$ | $C_9H_{19}$ |
| 36 | S | Se | $C_{10}H_{21}$ | $C_{10}H_{21}$ |
| 37 | S | Se | $C_{11}H_{23}$ | $C_{11}H_{23}$ |
| 38 | S | Se | $C_{12}H_{25}$ | $C_{12}H_{25}$ |
| 39 | S | S | cy-$C_6H_{11}$ | cy-$C_6H_{11}$ |
| 40 | S | S | cy-$C_8H_{15}$ | cy-$C_8H_{15}$ |
| 41 | S | S | cy-$C_{10}H_{19}$ | cy-$C_{10}H_{19}$ |
| 42 | S | S | cy-$C_{12}H_{23}$ | cy-$C_{12}H_{23}$ |
| 43 | S | S | cy-$C_5H_9C_2H_4$ | cy-$C_5H_9C_2H_4$ |
| 44 | S | S | cy-$C_5H_9C_3H_6$ | cy-$C_5H_9C_3H_6$ |
| 45 | S | S | $C_{10}H_{21}$ | cy-$C_6H_{11}$ |

A field effect transistor (hereinafter referred to as FET in some instances) of the present invention has two electrodes, i.e., a source electrode and a drain electrode, in contact with a semiconductor, and the current flowing between the electrodes is controlled by the voltage applied to another electrode referred to as a gate electrode.

Generally, a field effect transistor usually has a structure with a gate electrode isolated by an insulating film, i.e., a metal-insulator-semiconductor (MIS) structure. The structure having a metal oxide film as the insulating film is referred to as a MOS structure. Others include a structure having a gate electrode formed via a Schottky barrier, i.e., an MES structure. A FET with an organic semiconductor material usually has an MIS structure.

Referring to the drawings, an organic field effect transistor of the present invention will be more specifically described below. However, the present invention is not limited to these structures.

FIG. 1 shows schematic views illustrating field effect transistors (devices) according to several embodiments of the present invention. In each of the embodiments, reference number 1 represents a source electrode, 2 represents a semiconductor layer, 3 represents a drain electrode, 4 represents an insulating layer, 5 represents a gate electrode and 6 represents a substrate. The arrangement of individual layers and electrodes can be appropriately selected depending on purpose of the device. A to D each is referred to as a horizontal FET, because current flows in parallel to a substrate. A is referred to as a bottom-contact structure and B as a top-contact structure. Besides, C illustrates a structure commonly employed in manufacturing of an organic single-crystal FET, having source and drain electrodes and an insulating layer on a semiconductor with a gate electrode further formed thereon. D illustrates a structure referred to as a top & bottom-contact type transistor. E illustrates a schematic view of an FET having a vertical structure, i.e., a static induction transistor (SIT). In the SIT, a large amount of carriers can be transferred at a time, because current flow can spread in a two-dimensional way. In addition, since a source electrode and a drain electrode are vertically arranged, the distance between them can be reduced and thereby high-speed response is achieved. Accordingly, the SIT can be preferably used for supplying a large amount of current or performing high-speed switching. No substrate is shown in E of FIG. 1. However, substrates are usually provided outside the source and drain electrodes respectively indicated by reference numbers 1 and 3 in FIG. 1E.

Structural elements in each embodiment will be described.

The substrate 6 is required to retain layers formed thereon without detachment. Examples that can be used for the substrate 6 include an insulating material such as a resin board, a film, paper, glass, quartz and ceramic; a material having an insulating layer formed on a conductive substrate such as a metal or an alloy by a coating process or others; and a material composed of various combinations of a resin and an inorganic material. Examples of the resin film that can be used include polyethylene terephthalate, polyethylene naphthalate, polyether sulfone, polyamide, polyimide, polycarbonate, cellulose triacetate, and polyether imide. Using a resin film or a paper, the device can have pliability, resulting in enhanced flexibility, lightness and usefulness. The thickness of the substrate is usually 1 µm to 10 mm, preferably 5 µm to 5 mm.

For the source electrode 1, the drain electrode 3 and the gate electrode 5, a conductive material is used. Examples of the material include a metal such as platinum, gold, silver, aluminum, chromium, tungsten, tantalum, nickel, cobalt, copper, iron, lead, tin, titanium, indium, palladium, molybdenum, magnesium, calcium, barium, lithium, potassium or sodium, and an alloy containing them; a conductive oxide such as $InO_2$, $ZnO_2$, $SnO_2$ or ITO; a conductive polymer compound such as polyaniline, polypyrrole, polythiophene, polyacetylene, polyparaphenylene, vinylene or polydiacetylene; a semiconductor such as silicon, germanium and gallium arsenic; and a carbon material such as carbon black, fullerene, carbon nanotube or graphite. Furthermore, the conductive polymer and the semiconductor may have a dopant. Examples of the dopant include an inorganic acid such as hydrochloric acid and sulfuric acid; an organic acid having an acidic functional group such as sulfonic acid; a Lewis acid such as $PF_5$, $AsF_5$, or $FeCl_3$; a halogen atom such as iodine; and a metal atom such as lithium, sodium, or potassium. Boron, phosphorus, arsenic, or the like is commonly used as a dopant for an inorganic semiconductor such as silicon. Furthermore, a composite conductive material with carbon black or metal particles dispersed in the dopant may be used.

Source and drain electrodes each has a function of having direct contact with a semiconductor to inject electric charges such as electrons or holes into the semiconductor. In order to reduce the contact resistance and readily inject electric charges, it is important that the HOMO level or the LUMO level of the semiconductor is matched with work function of the electrode. In order to reduce the contact resistance for producing an ohmic device, it is also important that the metal electrode is doped or surface-modified with a material such as molybdenum oxide, tungsten oxide, or a thiol compound typified by hexafluorobenzenethiol.

The distance (channel length) between the source electrode and the drain electrode is an important factor for determining the characteristics of a device. The channel length is usually 0.1 µm to 300 µm, preferably 0.5 µm to 100 µm. While increased amount of current can be drawn with a short channel length, current leakage is adversely caused. Accordingly, an appropriate channel length is required. The width (channel width) between the source electrode and the drain electrode is usually 10 µm to 10000 µm, preferably 100 µm to 5000 µm. The channel width can be further extended with a comb-like electrode structure or the like. The channel width may be appropriately determined depending on a requisite current amount and a device structure.

The structure (shape) of each of the source electrode and the drain electrode will be described. The structures of the source and drain electrodes may be the same or different. In the case that a bottom-contact structure is employed, it is generally preferred to form each electrode into a rectangular parallelepiped by a lithographical process. The length of the electrode may be the same as the channel width mentioned above. The width of the electrode is not particularly limited. However, in order to reduce the area of a device, the width is preferably as short as possible provided that the electrical properties can be stabilized. The width of the electrode is usually 0.1 µm to 1000 µm, preferably 0.5 µm to 100 µm. The thickness of the electrode is usually 0.1 nm to 1000 nm, preferably 1 nm to 500 nm, and more preferably 5 nm to 200 nm. To each of electrodes 1, 3, and 5, wiring is connected. The wiring is made of a material nearly similar to that of the electrodes.

As the insulating layer 4, an insulating material is used. For example, the following may be used: a polymer such as polyparaxylylene, polyacrylate, polymethyl methacrylate, polystyrene, polyvinyl phenol, polyamide, polyimide, polycarbonate, polyester, polyvinyl alcohol, polyvinyl acetate, polyurethane, polysulfone, an epoxy resin, or a phenol resin, or a copolymer thereof; a fluorine resin such as a condensed fluorine polymer including a fluorine-containing acrylate resin and fluorine-containing polyimide, a fluorine-containing ether polymer, or a fluorine-containing cyclic ether polymer; a metal oxide such as silicon dioxide, aluminum oxide, titanium oxide or tantalum oxide; a ferroelectric metal oxide such as $SrTiO_3$ or $BaTiO_3$; a nitride such as silicon nitride or aluminum nitride; a sulfide; a dielectric substance such as fluoride; or a polymer containing dispersed particles of the dielectric substance. The film thickness of the insulating layer 4 depends on the material, and is usually 0.1 nm to 100 µm, preferably 0.5 nm to 50 µm, and more preferably 1 nm to 10 µm.

In the present invention, the compound represented by Formula (1) is used as the material of the semiconductor layer 2. Although the compound may be a mixture, the compound(s) represented by Formula (1) is contained in the semiconductor layer usually with an amount of 50 wt % or more, preferably 80 wt % or more, and further preferably 95 wt % or more.

In order to improve the characteristics of the field effect transistor or impart other characteristics, another type of organic semiconductor material and various additives may be added as required. Furthermore, the semiconductor layer 2 may have a multilayer structure.

In the field effect transistor of the present invention, at least one heterocyclic compound represented by Formula (1) is used as a semiconductor material. In fact, only the heterocyclic compound(s) represented by Formula (1) is preferably used as the semiconductor material. And, only the single heterocyclic compound represented by Formula (1) in particular, rather than a mixture of two or more of the heterocyclic compounds, is preferably used as the semiconductor material. However, in order to improve the transistor characteristics as mentioned above, additives such as a dopant may be added.

Such additives may be added usually within a range of 0.01 wt % to 10 wt %, preferably 0.05 wt % to 5 wt %, and more preferably 0.1 wt % to 3 wt % relative to the total amount of semiconductor materials.

Although the semiconductor layer may have a multilayer structure, a single layer structure is more preferred.

The thinner the film of the semiconductor layer 2 is, the more preferable it is as long as necessary functions are not impaired. This is because in a horizontal field effect transistor as shown in A, B or D, the characteristics do not depend on the thickness as long as it is at or above a certain level; whereas leaked current increases in many cases as the thickness increases. In order to exert necessary functions, the thickness of a semiconductor layer is usually 1 nm to 10 μm, preferably 5 nm to 5 μm, and more preferably 10 nm to 3 μm.

In the field effect transistor of the present invention, another layer may be provided as required, for example, between the substrate and the insulating film layer, between the insulating film layer and the semiconductor layer, or on the outer surface of the device. For instance, in the case that a protective layer is formed directly or via another layer on the semiconductor layer, atmospheric influence caused by humidity or the like can be reduced. Further, the electrical properties can be advantageously stabilized, and for instance the ON/OFF ratio of a device can be increased.

The materials for the protective layer are not specifically limited. For example, the followings are preferably used: a film made of a resin such as an epoxy resin, an acryl resin including polymethyl methacrylate, polyurethane, polyimide, polyvinyl alcohol, a fluorine resin, or a polyolefin; a film of inorganic oxide such as silicon oxide or aluminum oxide, a film of nitride such as silicon nitride; or a film of a dielectric nitride. In particular, a resin (polymer) with low permeability of oxygen or water or small water absorption is preferred. A protective material recently developed for an organic EL display can be also used. The thickness of the protective layer can be optionally selected depending on the intended use, and is usually 100 nm to 1 mm.

Furthermore, the film formability and the device characteristics can be improved by previously applying surface treatment onto the substrate or the insulating layer, on which the semiconductor layer is to be laminated. In particular, the characteristics of the organic semiconductor material may sometimes vary depending on the conditions of the film such as molecular orientation. For example, the characteristics of the film to be formed on the substrate can be improved by modifying, for example, the hydrophilicity/hydrophobicity of the substrate surface. In particular, the characteristics of the organic semiconductor material may sometimes greatly vary depending on the conditions of a film such as molecular orientation. Surface treatment of the substrate or the like can modify molecular orientation of the interface portion between the substrate or the like and the semiconductor layer to be formed thereon and reduce the number of trap sites on the substrate or the insulating layer, whereby, characteristics such as carrier mobility would be improved.

The trap site refers to a functional group such as a hydroxy group on an untreated substrate. In the case such the functional group exists there, electrons are attracted to the functional group, resulting in reduced carrier mobility. Accordingly, it is most often effective to reduce the number of trap sites in improving the characteristics such as carrier mobility.

Examples of such a substrate treatment for characteristic improvement include a hydrophobing treatment with hexamethyldisilazane, cyclohexene, octyltrichlorosilane, octadecyltrichlorosilane or the like; an acid treatment with hydrochloric acid, sulfuric acid, acetic acid or the like; an alkaline treatment with sodium hydroxide, potassium hydroxide, calcium hydroxide, ammonia or the like; an ozone treatment; a fluorination treatment; a plasma treatment with oxygen, argon or the like; formation of a Langmuir-Blodgett film; formation of a thin film of another insulator or a semiconductor; a mechanical treatment; an electrical treatment such as corona discharge; and a rubbing treatment with fibers or the like.

However, the field effect transistor with the compound of the present invention has a feature of not being susceptible to the material on the substrate or the insulating layer. This enables omission of more expensive treatments or conditioning of the surface and allows a wider variety of materials to be used, resulting in general versatility and reduction in cost.

In these embodiments, as a method for providing layers such as an insulating film layer and a semiconductor layer, for example a vacuum vapor deposition method, a sputtering method, a coating method, a printing method or a sol-gel method can be appropriately employed.

Next, a method for manufacturing the field effect transistor of the present invention will be described below by taking a bottom-contact type field effect transistor (FET) shown in embodiment A in FIG. 1 as an example with reference to FIG. 2.

The manufacturing method can be similarly applied also to field effect transistors in other embodiments mentioned above.

(Substrate and Substrate Treatment)

Figure 2:
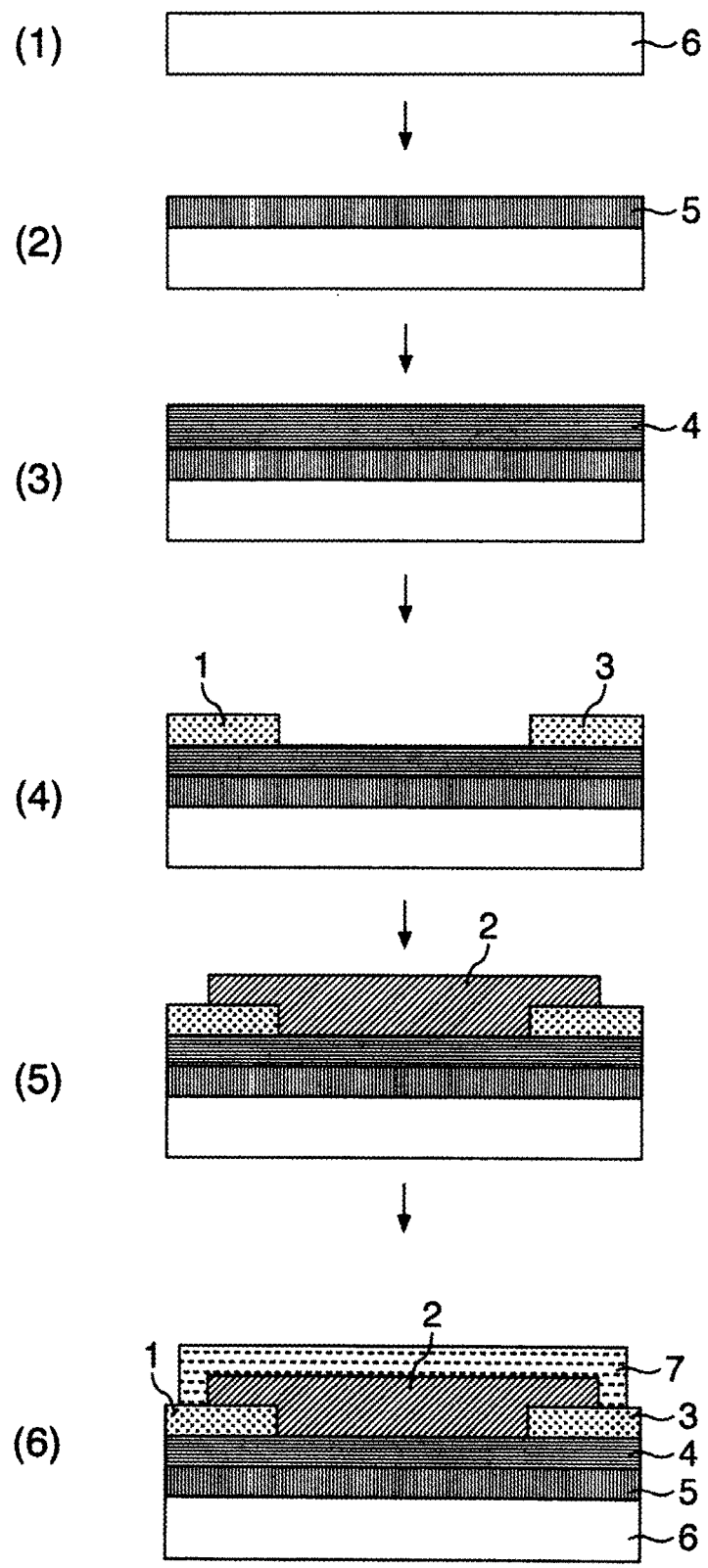
FIG. 2 shows schematic views illustrating the steps of manufacturing a field effect transistor according to an embodiment of the present invention.

The field effect transistor of the present invention is manufactured by providing various requisite layers and electrodes on the substrate 6 (see FIG. 2 (1)). As the substrate, those described above can be used. To the substrate, the aforementioned surface treatments can be also applied. The substrate 6 is preferably as thin as possible provided that necessary functions are not affected. The thickness is generally 1 μm to 10 mm, preferably 5 μm to 5 mm, depending on the material. Furthermore, if necessary, the substrate may also function as an electrode.

(Formation of Gate Electrode)

A gate electrode 5 is formed on the substrate 6 (see FIG. 2 (2)). As the material for the electrode, the one described above is used. Various methods can be used for forming an electrode film. For example, a vacuum vapor deposition method, a sputtering method, a coating method, a heat-transfer method, a printing method and a sol-gel method may be employed. Patterning may be preferably conducted as needed, during or after film formation so as to make a desired shape. Various types of patterning methods may be used. For example, photolithography with a combination of patterning and etching of a photoresist can be employed.

Alternatively, patterning can be conducted also by a printing method such as inkjet printing, screen printing, off-set printing and relief printing; a soft lithography such as micro-contact printing; and a combination method thereof. The thickness of the gate electrode 5 is usually 0.1 nm to 10 µm, preferably 0.5 nm to 5 µm, and more preferably 1 nm to 3 µm, depending on the material. In the case that a gate electrode also functions as a substrate, the thickness may be larger than the aforementioned film thickness.

(Formation of Insulating Layer)

An insulating layer 4 is formed on the gate electrode 5 (see FIG. 2 (3)). As the material for the insulator, the one described above or the like is used. The insulating layer 4 can be formed by various methods. Examples of the method include a coating method such as spin coating, spray coating, dip coating, cast coating, bar coating or blade coating; a printing method such as screen printing, off-set printing or inkjetting; or a dry-process method such as a vacuum vapor deposition method, a molecular beam epitaxial growth method, an ion cluster beam method, an ion plating method, a sputtering method, an atmospheric plasma method or a CVD method. Other examples include a sol-gel method and a method of forming an oxide film on a metal material, e.g., alumite on aluminum or a silicon dioxide on silicon.

At the portion at which an insulating layer and a semiconductor layer are in contact, a predetermined surface treatment can be applied to the insulating layer in order to properly orient molecules constituting a semiconductor, e.g., molecules of a heterocyclic compound represented by Formula (1), on the interface between the two layers. A method for the surface treatment may be the same as that to be applied to a substrate. The insulating layer 4 is preferably as thin as possible provided that the functions are not impaired. The thickness is usually 0.1 nm to 100 µm, preferably 0.5 nm to 50 µm, and more preferably 5 nm to 10 µm.

(Formation of Source Electrode and Drain Electrode)

A source electrode 1 and drain electrode 3 can be formed in the same manner as used for forming the gate electrode 5 (see FIG. 2 (4)).

(Formation of Semiconductor Layer)

As described above, an organic material containing one of the compounds represented by Formula (1) or a mixture of two or more of them, usually with a total amount of 50 wt % or more, is used as a semiconductor material. A semiconductor layer can be formed by various methods, which are roughly classified into a forming method by a vacuum process such as a sputtering method, a CVD method, a molecular beam epitaxial growth method and a vacuum vapor deposition method; and a forming method by a solution process such as a coating method including a dip coat method, a die coater method, a roll coater method, a bar coater and a spin coat method, an inkjet method, a screen printing method, an off-set printing method and a micro-contact printing method.

In the case that the semiconductor layer is formed with the heterocyclic compound represented by Formula (1) of the present invention as a semiconductor material, it is preferred to form the organic semiconductor layer by a vacuum process, and a vacuum vapor deposition method is further preferable. Since a film can be formed by a solution process, it is possible to employ an inexpensive printing method.

A method for producing the organic semiconductor layer by forming the organic material into a film by a vacuum process will be described.

In the present invention, a vacuum vapor deposition method is preferably employed. In the method, the organic material is heated under vacuum in a crucible or a metal boat, and the vaporized organic material is allowed to adhere (deposit) onto the substrate (exposed portions of an insulating layer, a source electrode and a drain electrode). On this occasion, the degree of vacuum is usually $1.0 \times 10^{-1}$ Pa or less and preferably $1.0 \times 10^{-3}$ Pa or less. Besides, because the characteristics of the organic semiconductor film and the field effect transistor therefrom may vary depending on the substrate temperature during deposition, it is necessary to select the substrate temperature carefully. The substrate temperature during deposition is usually 0° C. to 200° C., preferably 10° C. to 150° C., more preferably 15° C. to 120° C., further preferably 25° C. to 100° C., and particularly preferably 40° C. to 80° C.

Furthermore, the deposition rate is usually 0.001 nm/sec to 10 nm/sec, and preferably 0.01 nm/sec to 1 nm/sec. The thickness of the organic semiconductor layer made of the organic material is usually 1 nm to 10 µm, preferably 5 nm to 5 µm, and more preferably 10 nm to 3 µm.

The deposition method of heating and evaporating an organic material for forming a semiconductor layer and depositing the material onto the substrate may be replaced with a sputtering method of bombarding a target material with an accelerated ion such as argon to eject atoms of the material, thereby depositing the atoms onto the substrate.

Since the semiconductor material of the present invention is composed of the organic compound with a relatively low molecular weight, such a vacuum process may be preferably used. Although such a vacuum process requires slightly expensive equipment, the advantage is that a uniform film can be easily produced with good film formability.

Alternatively, a solution process or a coating method is preferably used in the present invention. The method will be described. In the present invention, the semiconductor material containing the heterocyclic compound represented by Formula (1) can be dissolved in the organic solvent and practical semiconductor characteristics are achieved by a solution process. An advantage of the production method by coating is that a large-area field effect transistor can be produced at low cost, because vacuum or high-temperature environment is not required during production.

Firstly, the heterocyclic compound represented by Formula (1) is dissolved in a solvent to prepare an ink for use in producing a semiconductor device. On this occasion, the solvent is not specifically limited, provided that the compound can be dissolved and a film can be formed on a substrate. Preferably the solvent is an organic solvent, and examples of the solvent that can be used include a halogeno hydrocarbon solvent such as chloroform, methylene chloride, or dichloroethane; an alcohol solvent such as methanol, ethanol, isopropyl alcohol, or butanol; a fluoro-alcohol solvent such as octafluoropentanol or pentafluoropropanol; an ester solvent such as ethyl acetate, butyl acetate, ethyl benzoate, or diethyl carbonate; an aromatic hydrocarbon solvent such as toluene, hexylbenzene, xylene, mesitylene, chlorobenzene, dichlorobenzene, methoxybenzene, chloronaphthalene, methylnaphthalene, or tetrahydronaphthalene; a ketone solvent such as acetone, methyl ethyl ketone, methyl isobutyl ketone, cyclopentanone, or cyclohexanone; an amide solvent such as dimethylformamide, dimethylacetamide, or N-methylpyrrolidone; an ether solvent such as tetrahydrofuran, diisobutyl ether, or diphenyl ether; and a hydrocarbon solvent such as octane, decane, decalin, or cyclohexane. These may be used alone or in mixtures.

For the purpose of improvement in film formability of the semiconductor layer or doping described below, an additive or other semiconductor material may be also mixed.

The principal examples of the additive include a polymer compound (e.g. an organic synthetic polymer compound, an organic natural polymer compound, or an inorganic polymer compound) or the like, and more specifically include a synthetic resin, a plastic, polyvinyl chloride, polyethylene, a phenol resin, an acrylic resin, an amide resin, an ester resin, nylon, vinylon, polyethylene terephthalate, synthetic rubber, polyisoprene, acrylic rubber, acrylonitrile rubber, and urethane rubber.

From the viewpoint of electric characteristics, these polymer materials are broadly classified into a conductive polymer compound, a semiconductor polymer compound, and an insulating polymer compound.

The conductive polymer compound is a polymer compound having a developed π electron skeleton in a molecule thereof to exhibit electrical conductivity. Examples of the conductive polymer compound include polyacethylene polymer, polydiacetylene polymer, polyparaphenylene polymer, polyaniline polymer, polytriphenylamine polymer, polythiophene polymer, polypyrrole polymer, polyparaphenylene vinylene polymer, polyethylene dioxythiophene polymer, a mixture of polyethylene dioxythiophene and polystyrene sulfonate (general name: PEDOT-PSS), nucleic acid, and a derivative thereof, most of which enhance conductivity by doping. Among these conductive polymer compounds, more preferred are polyacethylene polymer, polyparaphenylene polymer, polyaniline polymer, polytriphenylamine polymer, polythiophene polymer, polypyrrole polymer, polyparaphenylene vinylene polymer, and the like.

The semiconductor polymer compound is a polymer compound exhibiting semiconductivity. Examples of the semiconductor polymer compound include polyacethylene polymer, polydiacetylene polymer, polyparaphenylene polymer, polyaniline polymer, polytriphenylamine polymer, polythiophene polymer, polypyrrole polymer, polyparaphenylene vinylene polymer, polyethylene dioxythiophene polymer, nucleic acid, and a derivative thereof. Among these semiconductor polymer compounds, preferred are polyacethylene polymer, polyaniline polymer, polytriphenylamine polymer, polythiophene polymer, polypyrrole polymer, and polyparaphenylene vinylene polymer. The semiconductor polymer compound exhibits conductivity by doping, having conductivity depending on the amount of doping in some instances.

The insulating polymer compound is a polymer compound exhibiting insulation properties. Most polymer materials other than the conductive or semiconductor polymer materials described above are insulating polymer materials. Examples thereof are acrylic polymer, polyethylene polymer, polymethacrylate polymer, polystyrene polymer, polyethylene terephthalate polymer, nylon polymer, polyamide polymer, polyester polymer, vinylon polymer, polyisoprene polymer, cellulose polymer, copolymerized polymer and a derivative thereof.

The total concentration of the heterocyclic compounds represented by Formula (1) or the mixture thereof in the ink is usually in the range of about 0.001% to about 50%, preferably about 0.01% to about 20%, depending on the kind of solvent or film thickness of the semiconductor layer to be made.

For the use of ink, the semiconductor materials and the like containing the heterocyclic compound represented by Formula (1) and the like are dissolved in the solvent described above and, if necessary, solution heat treatment is performed. Furthermore, the solution is filtered with a filter or the like for removing solid content such as impurities to produce the ink for use in manufacturing a semiconductor device. The use of such ink enhances film formability of a semiconductor layer, which is preferable for making the semiconductor layer.

Subsequently, fine particles of the present invention will be described. The fine particles of the present invention usually have an average particle diameter of 5 nm or more and 50 µm or less, preferably 10 nm or more and 10 µm or less, and further preferably 20 nm or more and 5 µm or less. The fine particles with an excessively small average particle diameter may be easily affected by secondary aggregation, while an excessively large average particle diameter may cause lowering of stability of dispersion.

Subsequently, a method for producing the fine particles will be described. The heterocyclic compound of the present invention is dissolved in a solvent to produce a solution. The fine particles of the heterocyclic compound of the present invention are produced through precipitation by cooling the solution or mixing the solution with a separately prepared solvent.

The solvent for dissolving the compound of the present invention is not specifically limited, provided that the compound can be dissolved. Preferably the solvent is an organic solvent. More specifically, usable are a halogeno hydrocarbon solvent such as chloroform, methylene chloride, or dichloroethane; an alcohol solvent such as methanol, ethanol, isopropyl alcohol, or butanol; a fluoro-alcohol solvent such as octafluoropentanol or pentafluoropropanol; an ester solvent such as ethyl acetate, butyl acetate, ethyl benzoate or diethyl carbonate; an aromatic hydrocarbon solvent such as toluene, hexylbenzene, xylene, mesitylene, chlorobenzene, bromobenzene, dichlorobenzene, chlorotoluene, methoxybenzene, chloronaphthalene, methylnaphthalene, or tetrahydronaphthalene; a ketone solvent such as acetone, methyl ethyl ketone, methyl isobutyl ketone, cyclopentanone, or cyclohexanone; an amide solvent such as dimethylformamide, dimethylacetamide, or N-methylpyrrolidone; an ether solvent such as tetrahydrofuran, diisobutyl ether, or diphenyl ether; and a hydrocarbon solvent such as octane, decane, decalin, cyclohexane, dichloroethane, or chlorohexane. These may be used alone or in mixtures.

The precipitation can be performed by dissolving in the solvent described above or mixing with a separately prepared solvent that may be the same or different. In particular, using a solvent having a boiling point of 100° C. or more for dissolving, the precipitation is preferably performed through dissolving by heating and then mixing with a separately prepared solvent. On this occasion, preferably the solvent for dissolving the heterocyclic compound of the present invention has a boiling point of 100° C. or more, and more preferably is a hydrocarbon solvent. Examples of the solvent include an aromatic hydrocarbon solvent such as toluene, hexylbenzene, xylene, mesitylene, chlorobenzene, dichlorobenzene, methoxybenzene, chloronaphthalene, methylnaphthalene, or tetrahydronaphthalene; a hydrocarbon solvent such as octane, decane, decalin, or cyclohexane; and the like. Preferred is an aromatic hydrocarbon solvent such as toluene, xylene, dichlorobenzene, methylnaphthalene, or tetrahydronaphthalene. The use of these solvents is more effective, because each of these has a high boiling point, readily producing difference in solubility from at room temperature by heating.

The separately prepared solvent may be a solvent listed above, preferably a polar solvent including an alcohol solvent such as methanol, ethanol, isopropyl alcohol, or butanol; a fluoro-alcohol solvent such as octafluoropentanol or pentafluoropropanol; an ester solvent such as ethyl acetate, butyl acetate, ethyl benzoate or diethyl carbonate; a ketone solvent such as acetone, methyl ethyl ketone, methyl isobutyl ketone, cyclopentanone, or cyclohexanone; an amide solvent such as dimethylformamide, dimethylacetamide, or N-methylpyrrolidone. An alcohol solvent such as ethanol, isopropyl alcohol, or butanol, is particularly preferred with consideration for handling or the like.

Alternatively, the fine particles may be precipitated by dissolving the heterocyclic compound of the present invention in the solvent described above with heating to form a solution and then cooling the solution. On this occasion, the precipitation is more effectively performed with the solvent having a high boiling point, readily producing difference in solubility from at room temperature by heating. Also, fine particles are readily formed by cooling rapidly. The method for cooling is not specifically limited, including external cooling of the vessel containing the solution, rapid cooling by vaporizing heat through spray atomizing of the solution, and the like.

Also, a method for forming fine particles of pigments such as solvent milling, salt milling, acid pasting, acid slurrying, or the like may be appropriately used.

These fine particles are dispersed in a solvent to make dispersion, which can be the ink for use in manufacturing a semiconductor device. On this occasion, the solvent for use may be the solvent described in the paragraph on dissolving the heterocyclic compound of the present invention. It may be preferred to use the solvent for precipitating fine particles without treatment as a dispersion. The method for manufacturing dispersion is not specifically limited. Known methods are usually used as the method for manufacturing a dispersion, and particularly preferred is a dispersion method using mechanical stress. For example, included is a dispersion method using a kneader, an attritor, a roll mill, a bead mill, a paint shaker, a disperser, or the like. A stable dispersion is achieved by appropriately adding a dispersant, a dispersion aid, or the like during production, if necessary. For use as ink for use in manufacturing a semiconductor device, an additive, other semiconductor material, or the like may be mixed in the same way as in the substance described above.

Ink for use in manufacturing the semiconductor device can be prepared as mentioned above and is applied onto the substrate (exposed portions of an insulating layer, a source electrode and a drain electrode). A method of applying the ink includes a coating method such as casting, spin coating, dip coating, blade coating, wire bar coating and spray coating; a printing method such as inkjet printing, screen printing, off-set printing and relief printing; a soft lithographic method such as a micro-contact printing method; and a combination thereof.

Furthermore, the following may be employed as a method similar to the coating method: a Langmuir project method including the steps of dropping the ink onto a water surface to produce a monomolecular film of a semiconductor layer and transferring the film on a substrate for lamination; or a method of sandwiching a liquid crystal or a material in melt state between two substrates or introducing it into the space between the two substrates by capillary phenomenon.

The film thickness of the organic semiconductor layer manufactured by this method is preferably as thin as possible provided that functions are not impaired. The leaked current may increase with the increased film thickness. The thickness of the organic semiconductor layer is usually 1 nm to 10 μm, preferably 5 nm to 5 μm, and more preferably 10 nm to 3 μm.

The formed semiconductor layer (see FIG. 2 (5)) can be further improved in the characteristics by a post treatment. For instance, the characteristics can be improved and stabilized by heat treatment. The reasons are considered that by heat treatment, strain produced during film formation is relaxed, the number of pin holes is reduced, and alignment/orientation in the film can be controlled. Such the heat treatment is effective in manufacturing the field effect transistor of the present invention for improving the characteristics. The heat treatment is conducted by heating the substrate after the semiconductor layer is formed. The temperature for the heat treatment is not particularly limited, usually from room temperature to about 200° C., preferably 80° C. to 180° C., and further preferably 120° C. to 150° C. The time for the heat treatment is not particularly limited, usually 1 minute to 24 hours, preferably about 2 minutes to about 3 hours. The atmosphere for the treatment may be the air or an inert atmosphere such as nitrogen, argon or the like.

Furthermore, the following may be employed as another post treatment method: a treatment with an oxidizing or reducing gas such as oxygen or hydrogen, or with an oxidizing or reducing liquid, inducing a change in the characteristics with oxidation or reduction. In many cases, the method is used for increasing or decreasing the carrier density of a film, or others.

Furthermore, the characteristics of the semiconductor layer can be changed by adding small amounts of elements, atomic groups, molecules or polymers to the semiconductor layer in accordance with a method of so-called doping. For example, oxygen, hydrogen, an acid such as hydrochloric acid, sulfuric acid and sulfonic acid; a Lewis acid such as $PF_5$, $AsF_5$ and $FeCl_3$; a halogen atom such as iodine; a metal atom such as sodium and potassium can be employed for doping. The doping can be conducted by bringing such a gas into contact with a semiconductor layer, immersing a semiconductor layer in a solution, or subjecting a semiconductor layer to an electrochemical doping process. The doping may be conducted not only after a semiconductor layer is formed. The dopant may be added during synthesis of a semiconductor material. In the case that the semiconductor layer is formed by ink for use in manufacturing a semiconductor device, the dopant can be added to the ink. Further, the dopant can be added, for example, in a step of forming a precursor thin film disclosed in Patent Document 2. Furthermore, a material for doping may be added to a material for forming the semiconductor layer during deposition to achieve co-deposition, or a material for doping may be mixed with an ambient atmosphere used in forming the semiconductor layer to form the semiconductor layer under the environment containing the doping material. Furthermore, doping can be conducted by accelerating ions in vacuum and bombarding them to a film.

These doping methods result in a change in electrical conductivity due to an increased or decreased carrier density, a change in carrier polarity (p-type or n-type), a change in Fermi level or the like. Such doping is commonly used in a semiconductor device derived from an inorganic material, particularly, silicon or the like.

(Protective Layer)

Advantages of the formation of a protective layer 7 on the organic semiconductor layer are that influence of the outer air can be minimized and that the electrical characteristics of an organic field effect transistor can be stabilized (see FIG. 2 (6)). The material used for the protective layer 7 is the one described above.

The film thickness of the protective layer 7 may be appropriately determined, usually 100 nm to 1 mm, depending on an intended use.

Various methods may be employed for forming the protective layer. In the case that the protective layer is made of a resin, for example, a method of applying a resin solution and then drying it to form a resin film, or a method of applying or vapor depositing a resin monomer and then polymerizing the monomer can be employed. In addition, after the formation of the film, crosslinking treatment may be performed. In the case that the protective layer is made of inorganic substance, the following methods can be also used: a forming method by a vacuum process such as a sputtering method and a vapor deposition method; and a forming method by a solution process such as a sol-gel method.

In the field effect transistor of the present invention, the protective layer can be provided not only on the organic semiconductor layer but also between the layers, if necessary. These protecting layers may serve to stabilize the electrical characteristics of the organic field effect transistor in some instances.

In the present invention, since the organic material is used as a semiconductor material, a relatively low-temperature process can be employed in manufacturing. Accordingly, a flexible material such as a plastic plate or a plastic film that cannot be used in the conditions exposed to high temperature, can be also used as a substrate. As a result, an irrefrangible device with light weight and excellent flexibility can be manufactured and used as a switching element of an active matrix in a display, and others. Examples of the display include a liquid crystal display, a polymer dispersed liquid crystal display, an electrophoretic display, an EL display, an electrochromic display and a particle rotation display.

The field effect transistor of the present invention can be also used as a digital device or an analog device such as a memory circuit device, a signal driver circuit device and a signal processing circuit device. Furthermore, these can be used in combination to manufacture an IC card and an IC tag. Furthermore, since the characteristics of the field effect transistor of the present invention can be changed by an external stimulus such as a chemical substance, the use as an FET sensor is also achieved.

The operating characteristics of the field effect transistor are determined, for example, based on the carrier mobility and conductivity of the semiconductor layer, the capacitance of the insulating layer, the structure of the device (e.g., the distance between source and drain electrodes and the widths thereof, and the thickness of the insulating layer), and others. As a semiconductor material for the field effect transistor, the higher the carrier mobility of the resulting semiconductor layer, the more preferable the material is. The heterocyclic compound represented by Formula (1) has good film formability. Besides, although a pentacene derivative is labile in the air and difficult to handle, decomposing with moisture in the air, in the case that the heterocyclic compound represented by Formula (1) of the present invention is used as a semiconductor material, the resulting semiconductor layer has high stability and a long life after the formation. Since the compound is also stable in the air containing oxygen and water and in various kinds of solvents, steps of microparticulation, dispersion, or manufacturing of ink can be performed at low costs with stability. Besides, an advantage of the compound is that preservation stability of the ink can be achieved. Furthermore, a transistor having a semiconductor layer made of the heterocyclic compound represented by Formula (1) has a low threshold voltage. Accordingly, in the case that such a transistor is used in practice, a driving voltage is reduced, resulting in the reduced power consumption to save more energy compared to conventional ones. As a result, the transistor can be effectively used, for example, in a mobile display with a rechargeable battery, of which longer operation time is required. In addition, since the reduced threshold voltage reduces energy consumption and lowers an electric charge injection barrier from an electrode to a semiconductor film, it is also expected that durability of a semiconductor element and a semiconductor device having it is enhanced.

EXAMPLES

The present invention will be more specifically described by way of Examples below. However, the present invention should not be limited to these examples. In the Examples, unless otherwise specified, the term "parts" represents "parts by mass", "%" represents "% by mass", and "Compound No." represents "Compound No." in the Table 1.

The reaction temperature, unless otherwise specified, refers to the inner temperature of a reaction system.

Compounds produced in Synthesis Examples were subjected, as appropriate, to MS (mass spectrometry) and measurements of maximum absorption (λ max) and mp (melting point) to determine their structural formulas. Measurement apparatus are as follows.

MS spectrum: Shimadzu QP-5050A

Absorption spectrum: Shimadzu UV-3150

Synthesis Example 1

Synthesis of methyl 6-octynyl-2-naphthoate (100)

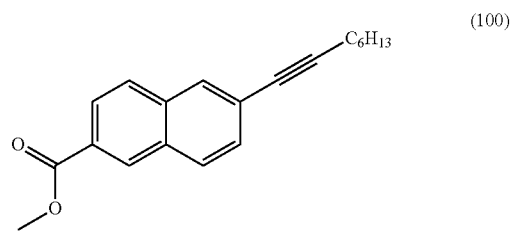

A 50 ml 3-neck flask having a reflux tube and a dripping funnel was substituted with nitrogen, and DMF (8 ml) was added thereinto and bubbled for 10 min. Into the 3-neck flask, methyl 6-bromo-2-naphthoate (1 g, 3.8 mmol), Pd(pph$_3$)$_4$ (218 mg, 0.12 mmol), NEt$_3$ (1.58 ml, 11.3 mmol), and CuI (36 mg, 0.19 mmol) were fed and stirred. Into the dripping funnel, toluene (8 ml) and 1-octyne (0.56 ml, 3.8 mmol) were fed, bubbled with Ar gas for 10 min, and then slowly dripped. Because raw materials still remained after stirring for 27.5 hours at room temperature, 1-octyne (0.28 ml, 1.9 mmol) was further added. After 4 hours, water and 2 N HCl were added so that the reaction was halted at ph 7. After extraction with methylene chloride, the organic phase was dried with anhydrous magnesium and filtered, and then the solvent was distilled away with a rotary evaporator. The reacted mixture produced was isolated and refined with silica gel column chromatography (3 cm in diameter×16 cm) using a methylene chloride solvent as a moving phase to produce an orange solid of methyl 6-octynylnaphthalenecarboxylate (1.02 g, 3.46 mmol, 92%).

A recrystallized sample from methylene chloride was used for measurement.

Methyl 6-octynyl-2-naphthoate: orange; $^1$H NMR (270 MHz, CDCl$_3$) δ0.92 (t, 3H, J=6.48 Hz), δ1.34~1.65 (m, 8H), δ2.46 (t, 2H, J=6.8 Hz) δ3.98 (s, 3H, CO$_2$CH$_3$) δ7.51 (dd, 1H, J=8.19, 1.32 Hz, ArH) δ7.80 (d, 1H, J=8.75, ArH) δ7.86 (d, 1H, J=8.47 Hz, ArH) δ7.92 (s, 1H, ArH) δ8.05 (dd, 1H, J=8.58, 1.49 Hz) EI-MS, m/z=294 (M$^+$)

Synthesis Example 2

Synthesis of methyl 6-octyl-2-naphthoate (101)

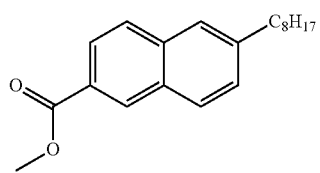

Into a 50 ml 3-neck flask, methyl 6-octynyl-2-naphthoate (100) (118 mg, 0.4 mmol) was fed and substitution with Ar gas performed. Then, 10% Pd/C (107 mg, 0.52 mmol) and toluene (25 ml) were added and dissolved. Using an aspirator, H$_2$ gas substitution was performed three times with stirring at room temperature for 2 hours. After completion of the reaction, filtration with celite was performed using hexane and the solvent was distilled away to produce a white solid of 6-octyl-naphthalene methyl carboxylate (107 mg, 0.36 mmol, 90%).

Methyl 6-octyl-2-naphthoate: white; $^1$H NMR (270 MHz, CDCl$_3$) δ0.87 (t, 3H, J=6.90 Hz), δ1.27~1.71 (m, 8H), δ2.79 (t, 2H, J=7.75 Hz) δ3.98 (s, 3H, CO$_2$CH$_3$) δ7.40 (dd, 1H, J=7.99, 1.66 Hz, ArH) δ7.65 (s, 1H, ArH) δ7.81 (d, 1H, J=8.2, ArH) δ7.87 (d, 1H, J=8.84 Hz, ArH) δ8.03 (dd, 1H, J=8.60, 1.75 Hz) ELMS, m/z=298 (M$^+$)

Synthesis Example 3

Synthesis of 2-hydroxymethyl-6-octylnaphthalene (102)

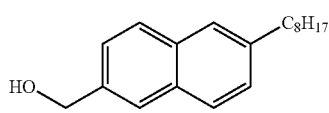

Into a 50 ml 3-neck flask, anhydrous THF (20 ml) and LAH (38 mg, 1 mmol) were added. While the flask was cooled in iced water, anhydrous THF (5 ml) solution of 6-octyl-naphthalene methyl carboxylate (101) (298 mg, 1 mmol) was slowly dripped. After stirring at room temperature for one hour, the reactant was fed into a beaker containing ice (30 ml to 40 ml) and 2 N HCL was added thereto. After complete separation of an organic phase and a water phase, extrusion and subsequent extraction with methylene chloride, the organic phase was dried with anhydrous magnesium. After filtration, the solvent was distilled away with a rotary evaporator to produce white 2-hydroxymethyl-6-octylnaphthalene (270 mg, 1 mmol, 100%).

2-Hydroxymethyl-6-octylnaphthalene: white; $^1$H NMR (270 MHz, CDCl$_3$) δ0.87 (t, 3H, J=6.53 Hz), δ1.26~1.72 (m, 8H), δ2.76 (t, 2H, J=7.71 Hz) δ4.85 (s, 2H, CH$_2$OH) δ7.35 (dd, 1H, J=8.53, 1.20 Hz, ArH) δ7.46 (dd, 1H, J=8.49, 1.67 Hz, ArH) δ7.61 (s, 1H, ArH) δ7.77 (3H, ArH) EI-MS, m/z=270 (M$^+$)

Synthesis Example 4

Synthesis of 6-octyl-2-naphthaldehyde (103)

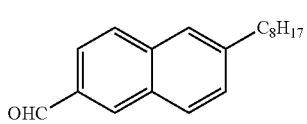

Into a 100 ml 3-neck flask, 2-hydroxymethyl-6-octylnaphthalene (102) (858 mg, 3.18 mmol) was fed to dissolve in CCl$_4$ (51 ml). MnO$_2$ (5.46 mg, 64 mmol) was added and reflux was performed for 20 hours. After cooling down to room temperature, insoluble solid was removed by filtering. The solvent was distilled away from the filtrate with a rotary evaporator. The reacted mixture produced was isolated and refined with silica gel column chromatography (3 cm in diameter×5 cm) using a methylene chloride solvent as a moving phase to produce a yellow oil of 6-octyl-2-naphthaldehyde (820 mg, 3.06 mmol, 94%).

6-Octyl-2-naphthaldehyde: yellow oil; $^1$H NMR (270 MHz, CDCl$_3$) δ0.88 (t, 3H, J=6.61 Hz), δ1.27~1.74 (m, 12H), δ2.81 (t, 2H, J=7.64 Hz) δ7.45 (dd, 1H, J=8.08, 1.66 Hz, ArH) δ7.68 (s, 1H, ArH) δ7.87 (d, 1H, J=8.52 Hz, ArH) δ7.93 (dd, 2H, J=8.39, 1.19 Hz, ArH) δ8.31 (s, 1H, ArH) δ10.14 (s, 1H, CHO) EI-MS, m/z=268 (M$^+$)

Synthesis Example 5

Synthesis of 3-methylthio-6-octyl-2-naphthaldehyde (104)

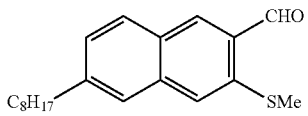

A 100 ml 3-neck flask having a dripping funnel was dried with heating and then the atmosphere thereof was substituted with nitrogen. Into the flask, N,N,N'-trimethyldiamine (0.93 ml, 7.3 mmol) and anhydrous THF (32 ml) were added and cooled at −30° C. Hexane solution of butyllithium (1.65 M, 4.4 ml, 7.3 mmol) was added thereto and stirred for 15 min. Subsequently anhydrous THF (30 ml) solution of 6-octyl-2-naphthaldehyde (103) (1.2 g, 4.5 mmol) was dripped at −30° C. for 5 min and stirred for 30 min. Further, hexane solution of butyllithium (1.65 M, 8.1 ml, 22 mmol) was added and stirred for 25 hours at −30° C. After dimethyl disulfide (1.35 ml, 15 mmol) was added at −30° C. and stirred at room temperature for 24 hours, 2 N hydrochloric acid was added and stirred for 24 hours. After extraction of the reacted solution with methylene chloride, the organic phase was dried with anhydrous magnesium and filtered, and then the solvent was distilled away with a rotary evaporator. The reacted mixture produced was refined with silica gel column chromatography using a mixed solvent of hexane:ethyl acetate at a ratio of 9:1 as a moving phase to produce a yellow solid of 3-methylthio-6-octyl-2-naphthaldehyde (815 mg, 2.6 mmol, 58%).

3-Methylthio-6-octyl-2-naphthaldehyde: yellow; $^1$H NMR (400 MHz, CDCl$_3$) δ0.88 (t, 3H, J=6.87 Hz), δ1.27~1.71 (m, 12H), δ2.59 (s, 3H, SMe) δ2.78 (t, 2H, J=7.68 Hz) δ7.35 (dd, 1H, J=8.46, 1.77 Hz, ArH) δ7.55 (s, 1H, ArH) δ7.57 (s, 1H, ArH) δ7.84 (d, 1H, J=8.35 Hz, ArH) δ8.29 (s, 1H) ELMS, m/z=314 (M$^+$)

Synthesis Example 6

Synthesis of 1,2-di(3-methylthio-6-octyl-2-naphthyl)ethylene (105)

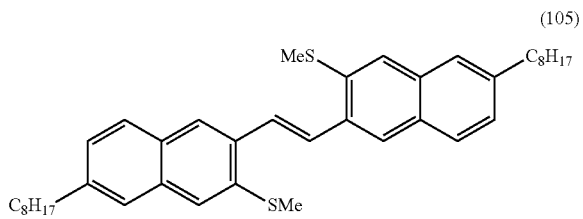

(105)

The inner atmosphere of a 500 ml 3-neck flask having a dripping funnel and a reflux tube was substituted with nitrogen and THF (300 ml) was fed therein. While the flask was cooled in an iced bath, TiCl$_4$ (5.6 ml, 51 mmol) was added. Zn (3.3 g, 51 mmol) was further fed therein and reflux was performed for 2 hours. Then, anhydrous THF solution (100 ml) of 3-methylthio-6-octyl-2-naphthaldehyde (104) (5.3 mg, 17 mmol) was slowly dripped, and anhydrous THF solution (10 ml) was further added to the dripping funnel. Then, reflux was performed for 28.5 hours. After cooling down to room temperature, saturated sodium carbonate aqueous solution and chloroform were added to turn the color of reaction system thoroughly. Then, insoluble solid was removed by filtering with celite. After extraction of the resultant filtrate with chloroform, the organic phase was dried with anhydrous magnesium and filtered, and then the solvent was distilled away with a rotary evaporator. From the yellow solid produced, components at the original point was removed with silica gel column chromatography using a CH$_2$Cl$_2$ solvent as a moving phase to produce a yellow solid of 1,2-di(3-methylthio-6-octyl-2-naphthyl)ethylene (105) (4.2 g, 7.0 mmol, 83%).

1,2-Di(3-methylthio-6-octyl-2-naphthyl)ethylene: yellow solid; $^1$H NMR (400 MHz, CDCl$_3$) δ0.88 (t, 6H, J=6.86 Hz), δ1.25~1.72 (m, 24H) δ2.59 (s, 6H, SMe) δ2.76 (t, 4H, J=7.57 Hz) δ7.28 (dd, 2H, J=8.3, 1.66 Hz, ArH) δ7.52 (s, 2H, ArH) δ7.59 (s, 2H, ArH) δ7.64 (s, 2H, ArH) δ7.76 (d, 2H, J=8.33 Hz, ArH) δ8.06 (s, 2H, ArH) EI-MS, m/z=596 (M$^+$)

Synthesis Example 7

Synthesis of 6,6'-dioctyldinaphtho[2,3-b:2',3'-f]thieno[3,2-b]thiophen (10)

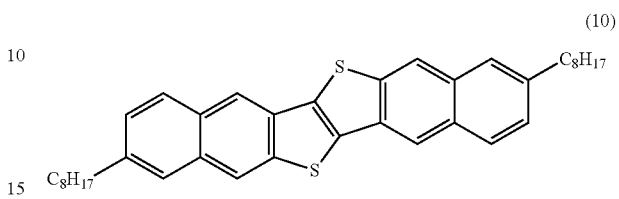

(10)

Into a 50 ml eggplant flask, 1,2-di(3-methylthio-6-octyl-2-naphthyl)ethylene (105) (314 mg, 0.53 mmol), iodine (4.0 g, 16 mmol), and CHCl$_3$ (22 ml) were added, and refluxed for 24.5 hours with a reflux tube. After cooled down to room temperature, saturated sodium hydrogen sulfite aqueous solution was added to turn the color thoroughly. Then, after extraction with CHCl$_3$, the organic phase was dried with anhydrous magnesium and filtered. Then the solvent was distilled away with a rotary evaporator. Subsequently, recrystallization was performed with CHCl$_3$ to produce a yellow solid (92 mg, 0.16 mmol, 31%).

Recrystallization was performed with chloroform to produce a yellow solid (10) (7 mg, 0.012 mmol, 15%).

6,6'-Dimethyldinaphtho[2,3-b:2',3'-f]thieno[3,2-b]thiophen: yellow solid; $^1$H NMR (270 MHz, CD$_2$Cl$_2$) δ0.88 (t, 6H, J=7.67 Hz), δ1.29-1.66 (m, 24H) δ2.85 (t, 4H) δ7.43 (dd, 2H, J=8.9, 1.39 Hz, ArH) δ7.74 (s, 2H, ArH) δ8.0 (d, 2H, J=8.17 Hz, ArH) δ8.36 (s, 2H, ArH) δ8.38 (s, 2H, ArH) EI-MS, m/z=368 (M$^+$) EI-MS, m/z=564 (M$^+$)

Thermal analysis (endothermic peak): 122, 240, 319, and 336° C. (using TG-DTA, nitrogen)

Synthesis Example 8

Compounds No. (6), (12), (14), and (106) were synthesized in the same way as described above.

6,6'-Dihexyldinaphtho[2,3-b:2',3'-f]thieno[3,2-b]thiophen (6)

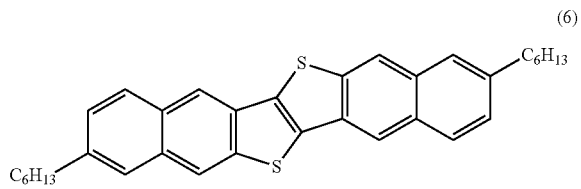

(6)

Yellow solid (yield: 34%)

$^1$H NMR (270 MHz, CDCl$_3$) δ0.90 (t, 6H, J=6.0 Hz), δ1.24~1.75 (m, 16H), δ2.83 (t, 4H, J=7.6 Hz) δ7.39 (dd, 2H, J=9.7, 1.6 Hz, ArH) δ7.70 (s, 2H, ArH) δ7.6 (d, 2H, J=8.8 Hz, ArH) δ8.32 (s, 2H, ArH) δ8.34 (s, 2H, ArH) EI-MS, m/z=508 (M$^+$)

Thermal analysis (endothermic peak): 134, 252, and 343° C. (using TG-DTA, nitrogen)

6,6'-Didecyldinaphtho[2,3-b:2',3'-f]thieno[3,2-b]thiophen (12)

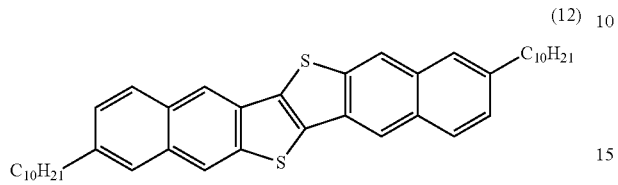

(12)

Yellow solid (yield: 43%)
$^1$H NMR (400 MHz, CDCl$_3$) δ0.90 (t, 6H, J=8.4 Hz), δ1.21~1.74 (m, 32H), δ2.79 (t, 4H, J=7.9 Hz) δ7.53 (dd, 2H, ArH) δ7.38 (s, 2H, ArH) δ7.95 (d, 2H, J=8.7 Hz, ArH) δ8.32 (s, 2H, ArH) δ8.34 (s, 2H, ArH) EI-MS, m/z=620 (M$^+$)
Thermal analysis (endothermic peak): 117, 219, and 298° C. (using TG-DTA, nitrogen)

6,6'-Didodecyldinaphtho[2,3-b:2',3'-f]thieno[3,2-b]thiophen (14)

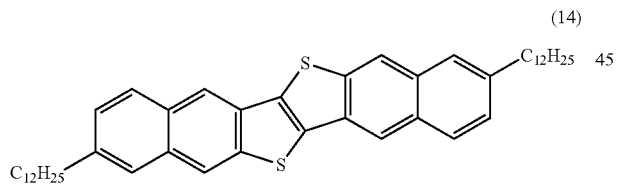

(14)

Thermal analysis (endothermic peak): 121, 210, 280, and 287° C. (using TG-DTA, nitrogen)

6,6'-Dibutyldinaphtho[2,3-b:2',3'-f]thieno[3,2-b]thiophen (106)

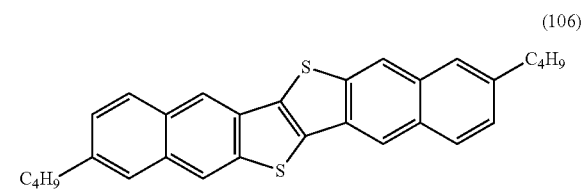

(106)

Thermal analysis (endothermic peak): 293 and 375° C. (using TG-DTA, nitrogen)

Note that Compound No. 106 corresponds to a comparative compound (ref. 2) in Example 1 and thereafter.

Synthesis Example 9

Compound No. 9 was synthesized also in the same way as shown in Synthesis Example 7 and theretofore.

6,6'-Bis(5''-methylhexyl)-dinaphtho[2,3-b:2',3'-f]thieno[3,2-b]thiophene (9)

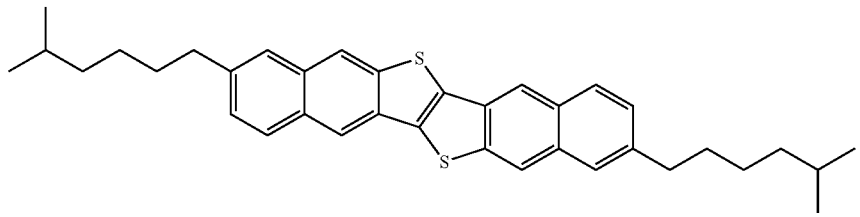

(9)

Yellow solid (yield: 32%), ELMS, m/z=536 (M$^+$)
Thermal analysis (endothermic peak): 275, 324 and 338° C. (using TG-DTA, nitrogen)

Example 1: Solubility Measurement

In Table 2, solubility (g/L) in toluene at 60° C. is listed.

TABLE 2

| Compound | R$^1$ and R$^2$ | Toluene |
|---|---|---|
| No. 6 | n-C$_6$H$_{13}$ | 0.08 |
| No. 10 | C$_8$H$_{17}$ | 0.06 |
| No. 12 | C$_{10}$H$_{21}$ | 0.05 |
| No. 14 | C$_{12}$H$_{25}$ | 0.04 |
| ref. 1 | H | not higher than 0.01 |
| ref. 2 | n-C$_4$H$_9$ | 0.02 |

As shown above, the introduction of an alkyl group enhanced solubility in an organic solvent, resulting in improvement in conditions corresponding to coating process.

Example 2 (Field Effect Transistor of Top-Contact Type)

An n-doped silicon wafer (surface resistance 0.02 Ω·cm or less) with a 300 nm-SiO$_2$ thermal oxidation film treated with hexamethylenedisilazane was placed in a vacuum vapor deposition apparatus and the apparatus was evacuated to a vacuum of 5.0×10$^{-3}$ Pa or less. Compound No. 10 was deposited on the electrode to a thickness of 50 nm by a resistive heating vapor deposition method at a substrate temperature of about 60° C. to form a semiconductor layer (2). Subsequently, a shadow mask for electrode formation was attached to the substrate and the substrate was placed in the vacuum vapor deposition apparatus. The apparatus was evacuated to a vacuum of $1.0\times10^{-4}$ Pa or less and gold electrodes, i.e., a source electrode (1) and a drain electrode (3) were deposited to a thickness of 40 nm by a resistive heating vapor deposition method to produce the field effect transistor of TC (top-contact) type of the present invention.

Figure 3:
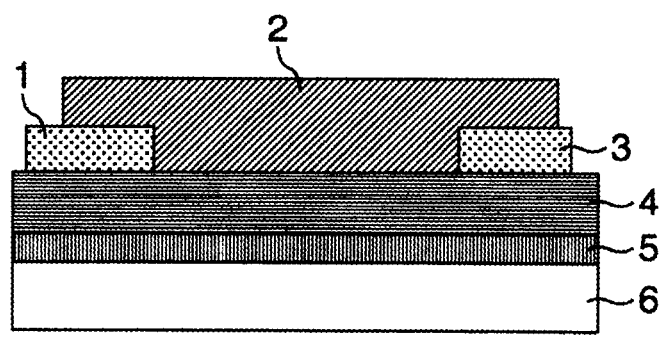
FIG. 3 shows a schematic view of the field effect transistor produced in Example 1 according to the present invention.

In the field effect transistor in this Example, the thermal oxidation film of the n-doped silicon wafer serves as an insulating layer (4) and the n-doped silicon wafer serves as not only a substrate (6) but also a gate electrode (5) (see FIG. 3).

The resultant field effect transistor was placed in a prober and the semiconductor characteristics were measured by a semiconductor parameter analyzer 4155C (manufactured by Agilent). As the semiconductor characteristics, drain current-drain voltage was measured by scanning gate voltage from 10V to −100V at the intervals of 20V, and scanning drain voltage from 10V to −100V. As a result, current saturation was observed. From the voltage-current curve obtained, it was found that the device was a p-type semiconductor having a carrier mobility of 3.1 cm$^2$/Vs and a threshold voltage of −10 V.

Example 3

The field effect transistor of TC type was produced in the same manner as in Example 2 except that Compound No. 10 used in Example 2 was replaced with various compounds. In Table 3, the results are shown.

TABLE 3

| Compound | R$^1$ and R$^2$ | Mobility |
| --- | --- | --- |
| No. 6 | n-C$_6$H$_{13}$ | 2.8 |
| No. 10 | C$_8$H$_{17}$ | 3.1 |
| No. 12 | C$_{10}$H$_{21}$ | 3.7 |
| ref. 1 | H | 1.2 |
| ref. 2 | n-C$_4$H$_9$ | 0.25 |

Using a vacuum process as in Example 2, various field effect transistors were produced. The characteristics thereof are highly excellent as a field effect transistor with normal organic substance as a semiconductor using a vapor deposition method. A distinctly high mobility was achieved with a vacuum vapor deposition method suitable for industrial application, and the level thereof is comparable to the mobility of a field effect transistor with a single crystal with low feasibility in industrial application. Due to the high performance of the field effect transistor of the present application, use in a wide variety of applications has been established, resulting in a significantly increased industrial value.

Example 4 (Characteristic Change in Field Effect Transistor with Substrate Treatment)

Surface treatments of n-doped silicon wafers with a 200 nm SiO$_2$ thermal oxidation film were performed with OTS-8 (octyltrichlorosilane), OTS-18 (octadecyloctadecylsilane), and HMDS (hexamethylenedisilazane), respectively. Vapor deposition was performed as in Example 2 on these substrates and a bare substrate to produce field effect transistors of TC type. The results of carrier mobility measured in the same manner are shown in the following Table.

Table 4

| | bare | OTS-8 | OTS-18 | HMDS |
| --- | --- | --- | --- | --- |
| ref. (R=H) | 0.2 | 2.9 | 3.0 | 1.2 |
| No. 6 (R=C$_6$H$_{13}$) | 0.9 | 1.1 | 4.0 | 2.8 |
| No. 10 (R=C$_8$H$_{17}$) | 2.3 | 3.3 | 3.0 | 3.1 |
| No. 12 (R=C$_{10}$H$_{21}$) | 3.8 | 3.8 | 5.4 | 3.7 |
| No. 14 (R=C$_{12}$H$_{25}$) | 2.1 | 2.1 | 3.2 | 1.3 |

As evidenced by the results of the experiments, although the mobility of a compound that is not substituted with an alkyl group is low with a substrate without surface treatment, the mobility is enhanced with surface treatment (from 0.2 to ten times or more with OTS). In contrast, the compounds substituted with a long linear alkyl group of the present invention exhibit high mobility even on the substrate without surface treatment. In particular, the compound No. 12 with OTS-18 has a highest mobility of 5.4 as a field effect transistor with a film formed by a vapor deposition method for an organic transistor, and further exhibits a distinctly high mobility of 3.8 even as an element on a substrate without surface treatment. This indicates that highly excellent semiconductor characteristics may be exhibited without depending on conditions of a substrate (insulating layer), and cost reduction in manufacturing or general use corresponding to various insulating films may be achieved. Accordingly, the industrial advantage is evident.

Example 5

An n-doped silicon wafer (surface resistance: 0.02 Ω·cm or less) with a 300 nm SiO$_2$ thermal oxidation film was coated with resist material, exposed for patterning, and 1-nm chromium and additional 40-nm gold were vapor deposited thereon. Subsequently, the resist was peeled off to form a source electrode (1) and a drain electrode (3). The silicon wafer with the electrodes was placed in a vacuum vapor deposition apparatus and the apparatus was evacuated to a vacuum of $5.0\times10^{-3}$ Pa or less. Compound No. 10 was vapor deposited on the electrode to a thickness of 50 nm by a resistive heating vapor deposition method at a substrate temperature of about 60° C. to form a semiconductor layer (2). Consequently, the field effect transistor of BC (bottom contact) type of the present invention was produced. In the field effect transistor in this Example, the thermal oxidation film of the n-doped silicon wafer with a thermal oxidation film serves as the insulating layer (4) and the n-doped silicon wafer serves as not only the substrate (6) but also the gate electrode (5) (see FIG. 3). The semiconductor characteristics were measured as in Example 2. As a result, current saturation was observed. From the voltage-current curve obtained, it was found that the device was a p-type semiconductor having a carrier mobility of 0.68 cm$^2$/Vs.

Example 6

After the field effect transistor of BC type produced in Example 5 was heat-treated at 150° C. in the air for 1 hour, the semiconductor characteristics were measured in the same manner. As a result, current saturation was observed. From the voltage-current curve obtained, it was found that the device was a p-type semiconductor having a carrier mobility of 1.00 cm$^2$/Vs.

Example 7

Field effect transistors of BC type were produced in the same manner as in Examples 5 and 6, except that various compounds were used instead of Compound No. 10 used in Example 5. In Table 5, the results are shown.

TABLE 5

| Compound | $R^1$ and $R^2$ | Mobility | Mobility after annealing |
|---|---|---|---|
| No. 10 | $C_8H_{17}$ | 0.68 | 1.0 |
| No. 14 | $C_{12}H_{25}$ | 0.3 | 2.3 |
| ref. 1 | H | 0.11 | 0.06 |
| ref. 2 | n-$C_4H_9$ | 0.10 | 0.01 |

It was shown that the field effect transistor of the present application exhibits a high mobility suitable for practical use even with bottom contact structure that usually tends to have poor characteristics. Furthermore, high thermal resistance is achieved and the mobility is even enhanced with heating. In contrast, in the case of a compound (ref. 2) having a C4 alkyl chain or a compound (ref. 1) having no alkyl group exhibited a reduced mobility after annealing. Since hot processes are present in manufacturing various devices, the compound needs to endure the heat. It was shown from the results that the compound having a long-chain alkyl group has excellent thermal resistance to the heat during manufacturing of the device.

Example 8

An n-doped silicon wafer (surface resistance: 0.02 Ω·cm or less) with a 300 nm $SiO_2$ thermal oxidation film was coated with resist material, exposed for patterning, and 1 nm chromium and additional 40 nm gold were vapor deposited thereon. Subsequently, the resist was peeled off to form a source electrode (1) and a drain electrode (3). A solution of 0.5% Compound No. 14 in 1,2-dichlorobenzene was prepared and heated to 100° C. to produce ink for use in manufacturing a semiconductor device. The silicon wafer having the electrodes was heated to 100° C. and the space between the electrodes was cast coated with the ink for use in manufacturing a semiconductor device to form a semiconductor layer (2). Consequently, the field effect transistor of BC (bottom contact) type of the present invention was produced. In the field effect transistor in this Example, the thermal oxidation film of the n-doped silicon wafer with a thermal oxidation film serves as the insulating layer (4) and the n-doped silicon wafer serves as not only the substrate (6) but also the gate layer (5) (see FIG. 3). The semiconductor characteristics were measured as in Example 1. As a result, current saturation was observed. From the voltage-current curve obtained, it was found that the device was a p-type semiconductor having a carrier mobility of 0.04 $cm^2$/Vs. Thus, semiconductor performance was confirmed. However, in the case of using comparative compound ref. 1 or ref. 2, each having extremely low solvent solubility, film forming was not achieved. As a result, no semiconductor layer was produced with a coating method.

As described above, the field effect transistor was produced using a solution process. Accordingly, it is evident that an organic semiconductor device can be produced by a printing method having potential for reducing cost.

Example 9

A channel region formed of an organic semiconductor thin film of an n-doped silicon wafer with a 200 nm $SiO_2$ thermal oxidation film treated with hexamethylenedisilazane (HMDS) was treated with ultraviolet irradiation through a mask, and HMDS was removed to form a lyophilic region. The lyophilic region was coated with 1-chloronaphthalene solution (200° C.) of Compound No. 10 by drop casting and dried at 60° C. to form a semiconductor thin film (2). Subsequently, the substrate was provided with a shadow mask for manufacturing electrodes and placed in a vacuum vapor deposition apparatus. The apparatus was evacuated to a vacuum of $1.0 \times 10^{-4}$ Pa or less, and gold electrodes, i.e., a source electrode (1) and a drain electrode (3) were deposited to a thickness of 50 nm by a resistive heating vapor deposition method to produce the field effect transistor of TC (top-contact) type of the present invention. The semiconductor characteristics were measured as in Example 1. As a result, current saturation was observed. From the voltage-current curve obtained, it was found that the device was a p-type semiconductor having a carrier mobility of 0.17 $cm^2$/Vs. Thus, semiconductor performance was confirmed. However, in the case of using comparative compound ref. 1 or ref. 2, each having extremely low solvent solubility, film forming was not achieved. As a result, no semiconductor layer was produced with a coating method.

As described above, an organic field effect transistor of coating type was produced using a self forming process, and a device exhibiting carrier mobility suitable for practical use was manufactured. Thereby the adaptability corresponding to various processes for manufacturing devices is achieved, and a wide variety of processes and applications may be used. Accordingly, the industrial advantage is evident.

Example 10

A yellow solid (93.1 mg) of Compound No. 12 ($R^1$ and $R^2$ each is $C_{10}H_{21}$) was dissolved in 95 ml of toluene with heating in the air to produce a colorless solution. The solution was dripped onto 2-propanol (600 ml, room temperature) while being strongly stirred to produce fine particles of the present invention. Then, the dispersion was once concentrated and 30 ml 2-propanol was added. Subsequently, the dispersion was further concentrated with an evaporator to produce a 1.02% dispersion (2-propanol solvent) of Compound No. 12. A silicon substrate was spin coated with the dispersion, and plate particles having an average particle diameter of 2 μm to 3 μm were observed with an optical microscope. No phase separation or the like was observed in the dispersion liquid after a lapse of 2 weeks.

Example 11

A yellow solid (93.1 mg) of Compound No. 12 ($R^1$ and $R^2$ each is $C_{10}H_{21}$) was dissolved in 95 ml of toluene with heating in the air to produce a colorless solution. The solution was injected to 2-propanol (300 ml) with a syringe to produce fine particles. Then, the dispersion was once concentrated and 30 ml 2-propanol was added. Subsequently, the dispersion was further concentrated with an evaporator to produce a 2.0% dispersion (2-propanol solvent) of Compound No. 12. A silicon substrate was spin coated with the dispersion, and plate particles having an average particle diameter of 200 nm were observed with an electron microscope.

Example 12

Tetralin (11.4 ml) was added to the 11.2 ml 2.0% dispersion of Compound No. 12 prepared in Example 11, which was concentrated with an evaporator to produce a 2.0% dispersion (tetralin solvent, boiling point: 207° C.) of Compound No. 12.

Example 13

The 3 ml 2.0% dispersion (tetralin solvent) of Compound No. 12 prepared in Example 12, 2-propanol (3 ml), and zirconia beads (30 μm, 4.8 g) were mixed and stirred with a stirring apparatus (7000 rpm, 30 min, ice chilled) to produce a 1.0% dispersion (1:1 tetralin/2-propanol solvent) of Compound No. 12.

Example 14

A yellow solid (93.1 mg) of Compound No. 12 ($R^1$ and $R^2$ each is $C_{10}H_{21}$) and polystyrene (manufactured by Aldrich, MW=350,000, 93.1 mg) were dissolved in 95 ml toluene to produce a 1.0% dispersion (PS content: 1.0%, 2-propanol solvent) of Compound No. 12 in the same manner as in Example 10.

Example 15

In Example 5, the field effect transistor of BC (bottom contact) type of the present invention was produced by forming a semiconductor layer (2) by vapor deposition. In contrast, in this Example, the semiconductor layer (2) was film-formed with spin coating with an ink (2-propanol solvent) for use in manufacturing a semiconductor device of 1.02% dispersion of Compound No. 12 as described in Example 10. The semiconductor characteristics were measured as in Example 2. As a result, current saturation was observed. From the voltage-current curve obtained, it was found that the device was a p-type semiconductor having a carrier mobility of $3.93 \times 10^{-2}$ cm$^2$/Vs, an ON/OFF ratio of $1.10 \times 10^6$, and a threshold voltage of −16.7 V.

Example 16

In the same manner as in Example 15, a semiconductor layer (2) was formed by spin coating with an ink (tetralin solvent, boiling point: 207° C.) for use in manufacturing a semiconductor device of 2.0% dispersion of Compound No. 12 produced in Example 12, and the film formed by spin coating was heat treated at 140° C. for 5 min. Consequently, the compound No. 12 dissolved on the silicon substrate to form a transparent thin film. The semiconductor characteristics were measured as in Example 2. As a result, current saturation was observed. From the voltage-current curve obtained, it was found that the device was a p-type semiconductor having a carrier mobility of $1.84 \times 10^{-2}$ cm$^2$/Vs.

Example 17 (Field Effect Transistor of Top Contact Type with Organic Insulating Film)

A film of polyimide resin solution (CT4112 manufactured by Kyocera Chemical Corporation) was formed on a washed ITO glass substrate (15Ω/□) by spin coating (4000 rpm×10 min). Under nitrogen atmosphere, the temperature was gradually raised and kept at 200° C. for 1 hour to form an organic insulating film on the ITO substrate. The substrate was placed in a vacuum vapor deposition apparatus and the apparatus was evacuated to a vacuum of $5.0 \times 10^{-3}$ Pa or less. Compound No. 12 was vapor deposited on the glass substrate having the organic insulating film to a thickness of 50 nm by a resistive heating vapor deposition method under conditions at a temperature of about 60° C. to form a semiconductor layer. Subsequently, the substrate was provided with a shadow mask for manufacturing electrodes and placed in a vacuum vapor deposition apparatus and the apparatus was evacuated to a vacuum of $1.0 \times 10^{-4}$ Pa or less. Then, gold electrodes, i.e., a source electrode (1) and a drain electrode (3) were vapor deposited to a thickness of 40 nm by a resistive heating vapor deposition method to produce the field effect transistor of TC (top-contact) type of the present invention.

In the field effect transistor in this Example, the polyimide resin serves as the insulating layer (4) and the ITO film on the glass substrate (6) serves as the gate electrode (5) (see FIG. 3).

The field effect transistor produced was placed in a prober and the semiconductor characteristics were measured by a semiconductor parameter analyzer 4155C (manufactured by Agilent). The semiconductor characteristics were measured at a drain voltage of −60 V by scanning gate voltage from 40V to −80V. From the voltage-current curve obtained, it was found that the device had a carrier mobility of 3.9 cm$^2$/Vs and a threshold voltage of −8 V.

As a result, the field effect transistor with an organic insulating film of the compound of the present invention had highly excellent characteristics, and the applicability to a flexible substrate or the like was validated.

As described in Example 1, using a compound such as No. 12 that can be applicable to a coating process, a dispersion liquid described in Example 10 or 11 is readily available in the air. In addition, as described in Example 12, a dispersion liquid may be prepared with 2-propanol to convert to a solvent having a higher boiling point with great ease. Furthermore, using the dispersion liquid (e.g. Example 12) with an once converted solvent having a high boiling point and the apparatus shown in Example 13 as required, not only a dispersion liquid having various compositions of two types of solvents but also a solvent composed of a combination of a plurality of solvents can be prepared in the same manner as in Example 13. Furthermore, through the use of an aromatic solvent such as toluene that easily dissolves various polymers including polystyrene, a dispersion liquid added with various polymers or compounds can be prepared as shown in Example 14.

REFERENCE SIGNS LIST

In FIG. 1 to FIG. 3, the same numerals denote the same components.
1 SOURCE ELECTRODE
2 SEMICONDUCTOR LAYER
3 DRAIN ELECTRODE
4 INSULATING LAYER
5 GATE ELECTRODE
6 SUBSTRATE
7 PROTECTING LAYER

The invention claimed is:
1. A heterocyclic compound represented by the following Formula (1):

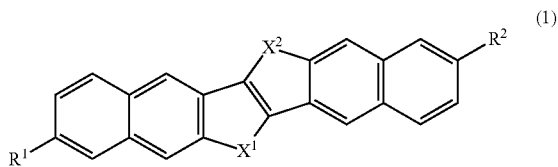

wherein $X^1$ and $X^2$ each independently represent a sulfur atom or a selenium atom, and $R^1$ and $R^2$ each independently represent a C6-C14 alkyl group.

2. The heterocyclic compound according to claim 1, wherein $R^1$ and $R^2$ of Formula (1) each independently represent a linear C6-C14 alkyl group.

3. The heterocyclic compound according to claim 1, wherein $R^1$ and $R^2$ of Formula (1) each independently represent a branched C6-C14 alkyl group.

4. The heterocyclic compound according to claim 1, wherein each of $X^1$ and $X^2$ of Formula (1) represents a sulfur atom.

5. A method for producing an intermediate compound represented by Formula (B) in producing a heterocyclic compound represented by the following Formula (1), comprising the steps of:
mixing a compound represented by Formula (A) with an alkyl metal reagent such as butyllithium; and
further adding dimethyl disulfide, or selenium and methyl iodide thereto:

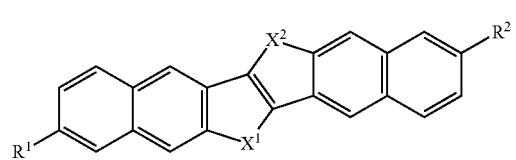
(1)

wherein $X^1$ and $X^2$ each independently represent a sulfur atom or a selenium atom, and $R^1$ and $R^2$ each independently represent a C6-C14 alkyl group;

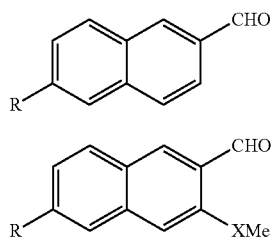
(A)
(B)

wherein X represents a sulfur atom or a selenium atom, and R represents a C6-C14 alkyl group.

6. A method for producing the heterocyclic compound represented by the following Formula (1) according to claim 1, comprising the steps of:
reacting intermediates represented by Formula (B) with one another to produce a compound represented by Formula (C); and
subsequently reacting the compound represented by Formula (C) with iodine:

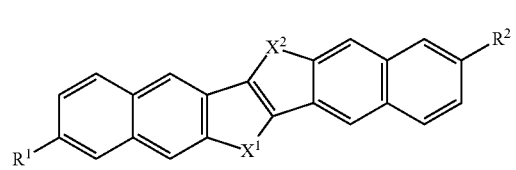
(1)

wherein $X^1$ and $X^2$ each independently represent a sulfur atom or a selenium atom, and $R^1$ and $R^2$ each independently represent a C6-C14 alkyl group;

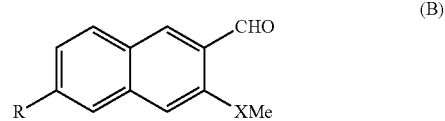
(B)

wherein X represents a sulfur atom or a selenium atom, and R represents a C6-C14 alkyl group;

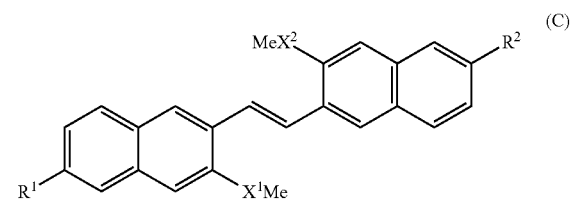
(C)

wherein $X^1$ and $X^2$ each independently represent a sulfur atom or a selenium atom, and $R^1$ and $R^2$ each independently represent a C6-C14 alkyl group.

7. An organic semiconductor material comprising at least one heterocyclic compound according to claim 1.

8. An ink for use in producing a semiconductor device, comprising the heterocyclic compound according to claim 1.

9. A field effect transistor having a semiconductor layer comprising at least one heterocyclic compound represented by the following Formula (1):

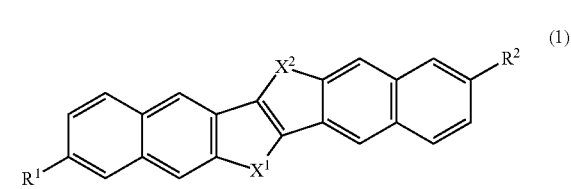
(1)

wherein $X^1$ and $X^2$ each independently represent a sulfur atom or a selenium atom, and $R^1$ and $R^2$ each independently represent a C6-C14 alkyl group.

10. The field effect transistor according to claim 9, wherein the field effect transistor is of bottom-contact type.

11. The field effect transistor according to claim 9, wherein the field effect transistor is of top-contact type.

12. The field effect transistor according to any one of claims 9 to 11, further comprising a gate electrode, a gate insulating film, a source electrode, and a drain electrode, wherein the gate insulating film is an organic insulating film.

13. A method for producing a field effect transistor, comprising the step of forming a semiconductor layer comprising at least one heterocyclic compound represented by the following Formula (1) on a substrate:

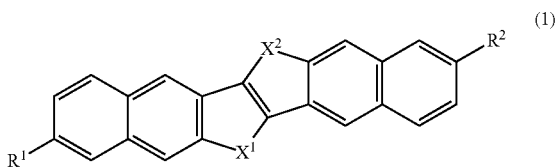

wherein $X^1$ and $X^2$ each independently represent a sulfur atom or a selenium atom, and $R^1$ and $R^2$ each independently represent a C6-C14 alkyl group.

14. The method for producing the field effect transistor according to claim 13, wherein the semiconductor layer is formed by a vapor deposition method.

15. The method for producing the field effect transistor according to claim 13, wherein the semiconductor layer is formed by applying the heterocyclic compound represented by the following Formula (1) dissolved in an organic solvent:

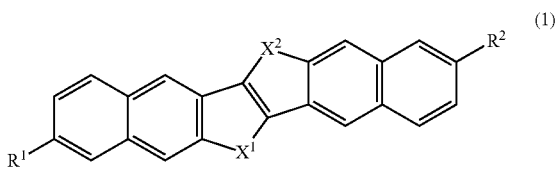

wherein $X^1$ and $X^2$ each independently represent a sulfur atom or a selenium atom, and $R^1$ and $R^2$ each independently represent a C6-C14 alkyl group.

16. The method for producing the field effect transistor according to any one of claims 13 to 15, wherein the semiconductor layer is heat-treated, after the semiconductor layer is formed.

17. A fine particle of the heterocyclic compound represented by Formula (1) according to claim 1.

18. The fine particle according to claim 17, wherein the average particle diameter is 5 nm or more and 50 μm or less.

19. A method for producing the fine particle according to claim 17 or 18, wherein the fine particle is precipitated by cooling a solution of the heterocyclic compound dissolved in an organic solvent or by mixing the solution with a solvent.

20. The method for producing the fine particle according to claim 17 or 18, wherein the fine particle is precipitated by mixing a solution of the heterocyclic compound dissolved in an organic solvent with a polar solvent.

21. The method for producing the fine particle according to claim 19, wherein the organic solvent for dissolving the heterocyclic compound has a boiling point of 100° C. or more.

22. A dispersion of the fine particle of the heterocyclic compound, wherein the fine particle according to claim 17 or 18 is dispersed in a solvent.

23. A method for producing the dispersion according to claim 22, wherein the method comprises the step of dispersing the fine particle in a solvent by mechanical stress.

24. An ink for use in producing a semiconductor device, comprising the dispersion according to claim 22.

25. A method for producing a field effect transistor comprising a step of forming a semiconductor layer by applying the ink for use in producing the semiconductor device according to claim 24.

26. The method for producing the field effect transistor according to claim 25, wherein the semiconductor layer is heat-treated, after the semiconductor layer is formed.

27. The heterocyclic compound according to claim 1, wherein $R^1$ and $R^2$ of Formula (1) each independently represent a linear C6-C12 alkyl group.

28. The method for producing a field effect transistor according to claim 5, wherein $R^1$ and $R^2$ of Formula (1) each independently represent a linear C6-C12 alkyl group.

* * * * *